US012631626B2

(12) United States Patent
Soh et al.

(10) Patent No.: US 12,631,626 B2
(45) Date of Patent: May 19, 2026

(54) CONTINUOUS REAL-TIME MONITORING OF BIOMOLECULES IN LIVE SUBJECTS

(71) Applicant: CZ BIOHUB SF, LLC, San Francisco, CA (US)

(72) Inventors: Hyongsok Soh, Stanford, CA (US); Mahla Poudineh, Stanford, CA (US); Jing Pan, Stanford, CA (US)

(73) Assignees: THE BOARD OF TRUSTEES OF THE LELAND STANFORD JUNIOR UNIVERSITY, Stanford, CA (US); CZ BIOHUB SF, LLC, San Francisco, CA (US)

( * ) Notice: Subject to any disclaimer, the term of this patent is extended or adjusted under 35 U.S.C. 154(b) by 913 days.

(21) Appl. No.: 17/793,205

(22) PCT Filed: Jan. 15, 2021

(86) PCT No.: PCT/US2021/013715
§ 371 (c)(1),
(2) Date: Jul. 15, 2022

(87) PCT Pub. No.: WO2021/146612
PCT Pub. Date: Jul. 22, 2021

(65) Prior Publication Data
US 2023/0061218 A1 Mar. 2, 2023

Related U.S. Application Data

(60) Provisional application No. 62/962,646, filed on Jan. 17, 2020.

(51) Int. Cl.
*G01N 33/543* (2006.01)
*A61B 5/00* (2006.01)
(Continued)

(52) U.S. Cl.
CPC ..... *G01N 33/54366* (2013.01); *A61B 5/0071* (2013.01); *A61B 5/0077* (2013.01);
(Continued)

(58) Field of Classification Search
CPC ...... A01N 25/28; A01N 37/18; A61B 5/0071; A61B 5/0077; A61B 5/14532;
(Continued)

(56) References Cited

U.S. PATENT DOCUMENTS

2013/0011849 A1* 1/2013 Henkin ................ G01N 33/543
435/7.1
2016/0166186 A1 6/2016 Ferguson et al.
(Continued)

FOREIGN PATENT DOCUMENTS

WO 2019/236548 A1 12/2019

OTHER PUBLICATIONS

Arroyo-Curras et al., Real-time measurement of small molecules directly in awake, ambulatory animals, PNAS, 114(4):645-650 (2016).
(Continued)

*Primary Examiner* — Jennifer Wecker
*Assistant Examiner* — Jonathan Bortoli
(74) *Attorney, Agent, or Firm* — MARSHALL, GERSTEIN & BORUN LLP

(57) ABSTRACT

The present disclosure provides materials and methods for the continuous measurement of biomolecules in vivo and in real-time. The present disclosure relates more specifically to using capture agents and detection agents within a microfluidic device to detect and quantify biochemical features of biomarkers, enabling real-time detection and concentration measurements.

20 Claims, 13 Drawing Sheets

Specification includes a Sequence Listing.

(51) Int. Cl.
  *A61B 5/145*    (2006.01)
  *A61B 5/1455*   (2006.01)
  *A61B 5/1486*   (2006.01)
(52) U.S. Cl.
  CPC ........ *A61B 5/14532* (2013.01); *A61B 5/1455*
     (2013.01); *A61B 5/14535* (2013.01); *A61B*
     *5/14865* (2013.01); *C12N 2310/16* (2013.01);
     *C12N 2310/3517* (2013.01); *G01N 2470/04*
                                        (2021.08)
(58) Field of Classification Search
  CPC ............ A61B 5/14535; A61B 5/14542; A61B
     5/1455; A61B 5/14865; A61B 5/686;
     A61K 2800/412; A61K 8/046; A61K
     8/11; A61K 8/25; A61K 8/37; A61K
     8/375; A61K 8/43; A61K 8/65; A61K
     8/84; A61K 8/87; A61K 9/0014; A61K
     9/06; A61K 9/4808; A61K 9/4816; A61K
     9/5005; A61K 9/5031; A61Q 13/00;
     A61Q 15/00; A61Q 19/00; B01J 13/203;
     C11D 17/0013; C11D 17/0039; C11D
     2111/12; C11D 3/0015; C11D 3/43; C11D
     3/505; C11D 7/5022; C12N 2310/16;
     C12N 2310/3517; D06M 13/005; D06M
     2200/50; D06M 23/06; D06M 23/12;
     G01N 2470/04; G01N 33/54366
  See application file for complete search history.

(56)            References Cited

U.S. PATENT DOCUMENTS

2019/0184395 A1*  6/2019  Ros ......................... B03C 5/028
2020/0041501 A1*  2/2020  Konry ............. G01N 33/54313
2022/0170077 A1*  6/2022  Church ................ C12Q 1/6804

OTHER PUBLICATIONS

Chang et al., Construction of a Multiple-Aptamer-Based DNA Logic Device on Live Cell Membranes via Associative Toehold Activation for Accurate Cancer Cell Identification, JACS, 141(32):12738-12743 (2019).
Chin et al., Microfluidics-based diagnostics of infectious diseases in the developing world, Nat. Med., 17(8):1015-9 (2011).
Choi et al., Immuno-hybridization chain reaction for enhancing detection of individual cytokine-secreting human peripheral mononuclear cells, Anal. Chem., 83(17):6890-6895 (2011).
Ferguson et al., Real-time, aptamer-based tracking of circulating therapeutic agents in living animals, Sci. Transl. Med., 5(213):213ra165 (2013).
Hovorka, Continuous glucose monitoring and closed-loop systems, Diabetic Medicine, 23(1):1-12 (2006).
International Application No. PCT/US2021/013715, International Preliminary Report on Patentability, mailed Jul. 28, 2022.
International Application No. PCT/US2021/013715, International Search Report and Written Opinion, mailed Jun. 8, 2021.
International Application No. PCT/US2021/013715, Invitation to Pay Additional Fees, mailed Apr. 14, 2021.
Kahanovitz et al., Development of a Microsphere-Based System to Facilitate Real-Time Insulin Monitoring, J. Diabetes Science and Technology, 10(3):689-696 (2016).
Koos et al., Proximity-dependent initiation of hybridization chain reaction, Nature Comm., 6:7294 (2015).
Lee et al., A fully automated immunoassay from whole blood on a disc, Lab Chip, 9(11):1548-1555 (2009).
Li et al., Proximity-induced hybridization chain assembly with small-molecule linked DNA for single-step amplified detection of antibodies, Chem Comm., 55(30):4387-4390 (2019).
Liu et al., A fully integrated distance readout ELISA-Chip for point-of-care testing with sample-in-answer-out capability, Biosens. Bioelectron., 96:332-338 (2017).
Marschewski et al., Mixing with herringbone-inspired microstructures: overcoming the diffusion limit in co-laminar microfiber devices, Lab Chip, 15(8):1923-1933 (2015).
McGrath et al., Deterministic lateral displacement for particle separation: a review, Lab Chip, 14(21):4139-4158 (2014).
Ranallo et al., Orthogonal regulation of DNA nanostructure self-assembly and disassembly using antibodies, Nature Comm., 10(1):5509 (2019).
Sun et al., ELISA-LOC: lab-on-a-chip for enzyme-linked immunodetection, Lab Chip, 10(16):2093-2100 (2010).
Tang et al., Universal strategy to engineer catalytic DNA hairpin assemblies for protein analysis, Anal. Chem., 87(16):8063-8066 (2015).
Wang et al., Imaging of Receptor Dimers in Zebrafish and Living Cells via Aptamer Recognition and Proximity-Induced Hybridization Chain Reaction, Anal. Chem., 90(24):14433-14438 (2018).
Weng et al., Rapid Detection of Food Allergens by Microfluidics ELISA-Based Optical Sensor, Biosensors, 6(2):24 (2016).

* cited by examiner

*Glucose probe validation*

*Insulin probe validation*

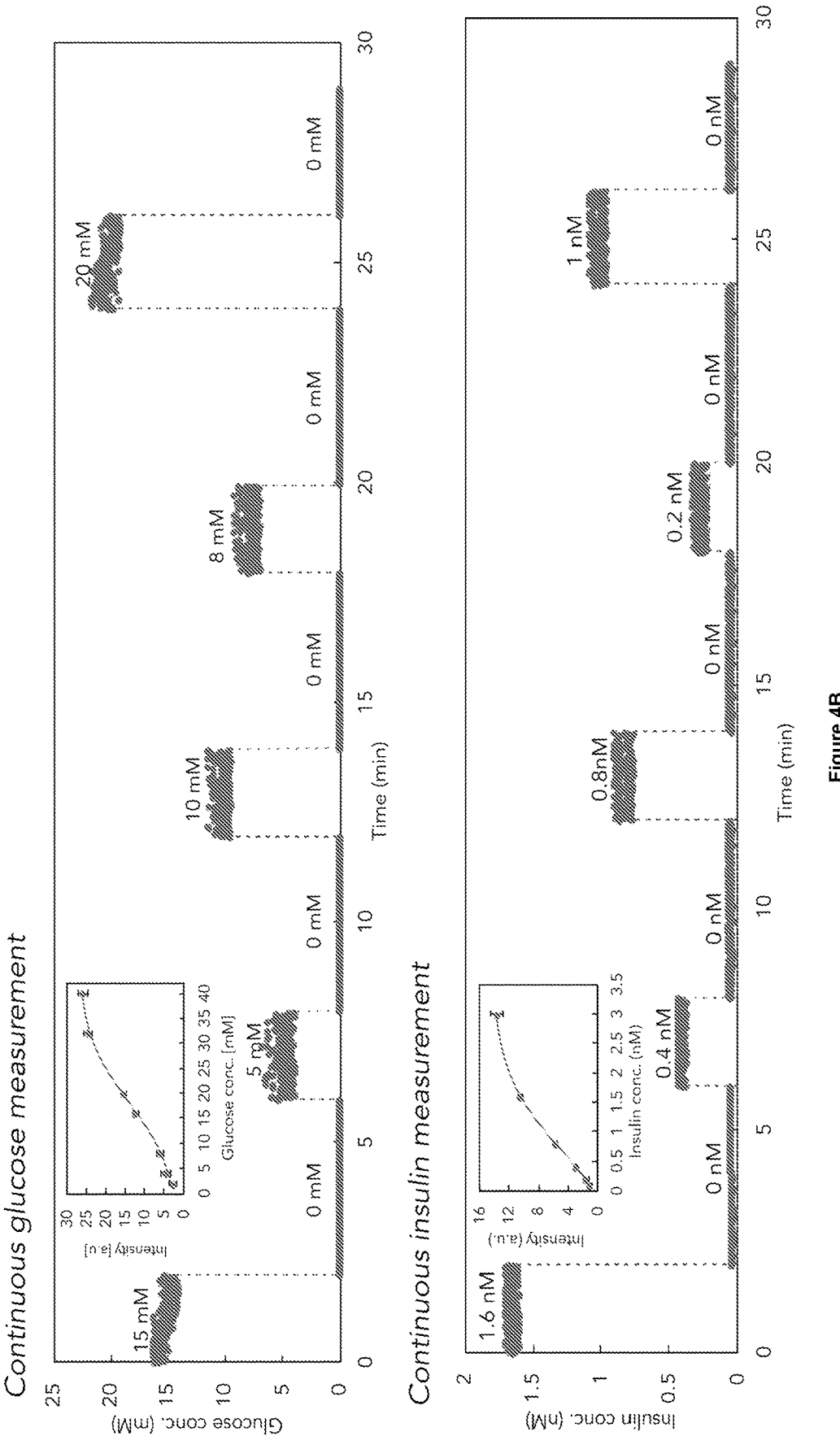

Figure 7A *Glucose measurement-Humulin R injection*
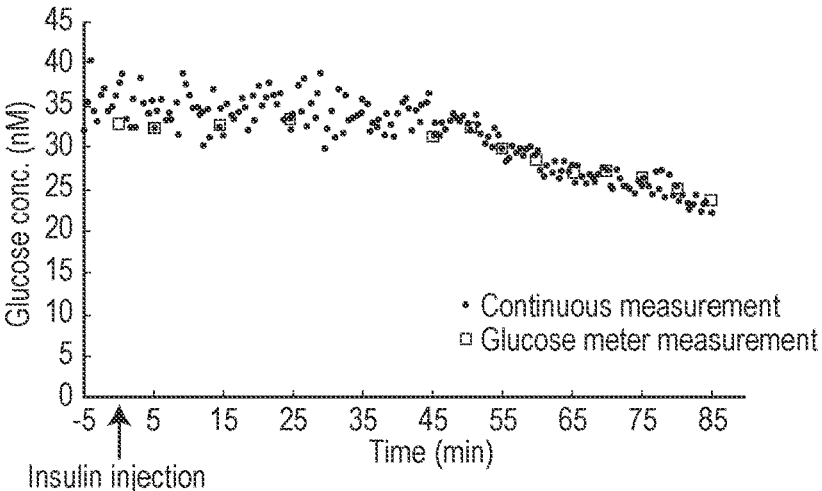
Figure 7B *Glucose measurement-Humulin N injection*
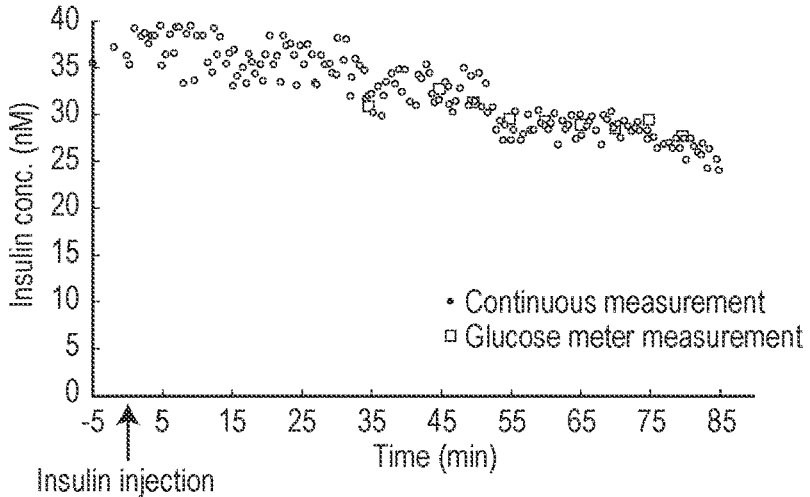
Figure 7C *Insulin measurement*
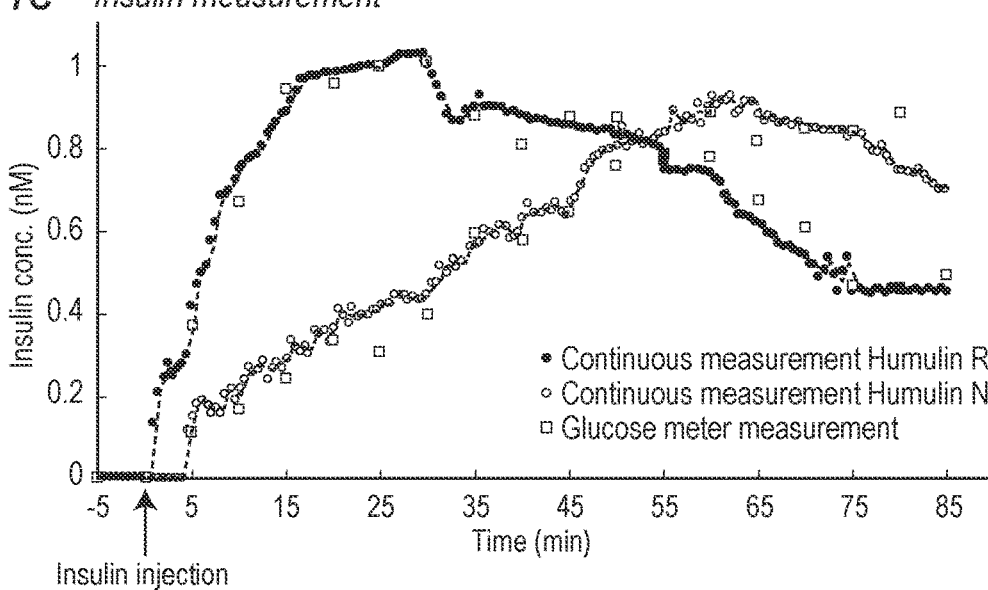

Figure 9

Figure 10
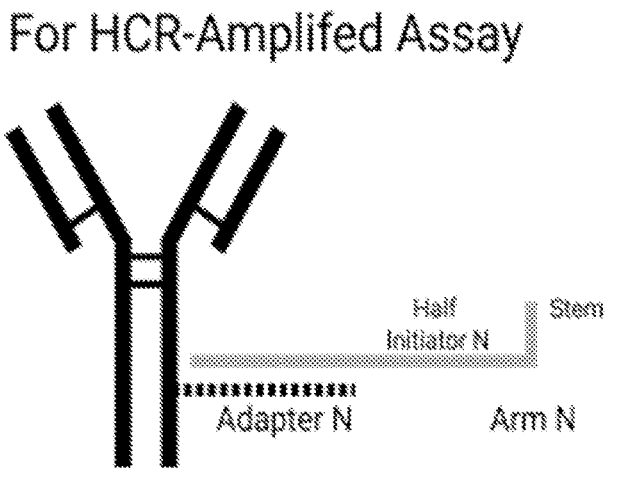
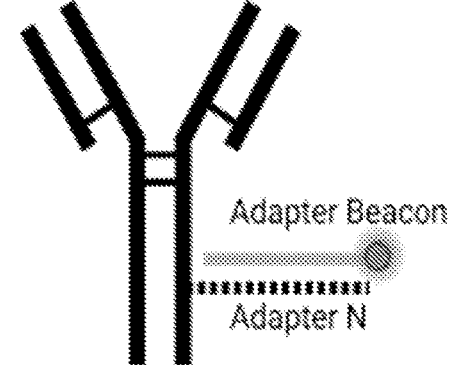

CONTINUOUS REAL-TIME MONITORING OF BIOMOLECULES IN LIVE SUBJECTS

CROSS-REFERENCE TO RELATED APPLICATIONS

This application is a U.S. National Phase of International Patent Application No. PCT/US2021/013715 filed Jan. 15, 2021, which claims the benefit of U.S. Provisional Patent Application No. 62/962,646 filed on Jan. 17, 2020. The entire contents of these applications are incorporated herein by reference in their entirety.

STATEMENT REGARDING FEDERALLY SPONSORED RESEARCH

This invention was made with Government support under contract DK116074 awarded by the National Institutes of Health. The Government has certain rights in the invention.

INCORPORATION BY REFERENCE OF MATERIAL SUBMITTED ELECTRONICALLY

The Sequence Listing, which is a part of the present disclosure, is submitted concurrently with the specification as a text file. The name of the text file containing the Sequence Listing is "54752A_Seqlisting.txt", which was created on Jul. 14, 2022 and is 1,808 bytes in size. The subject matter of the Sequence Listing is incorporated herein in its entirety by reference.

FIELD

The present disclosure relates generally to methods for the continuous measurement of specific biomolecules in vivo. The present disclosure relates more specifically to using sensors within microfluidic devices to detect and quantify biochemical features of biomarkers, enabling real-time detection and concentration measurements.

BACKGROUND

A continuous monitoring device capable of constantly measuring one or more biomolecules has the potential to revolutionize the healthcare system by enabling truly personalized medicine. Such technology would allow physicians to tailor specific drug and medical treatments to an individuals' unique molecular profile, facilitating more effective treatment and therapeutics.

Despite the considerable medical values that can be introduced by continuous molecular monitoring, to date it has only been realized for a handful of analytes that produce readily-measurable signals from analyte-specific reactions. For example, detection of glucose through glucose oxidase activity in continuous glucose meters (CGMs) has been developed (Hovorka, Diabetic Medicine, 23(1):2006). Indeed, CGMs have become standard in diabetes management. Recently, the availability of insulin pumps and CGMs have culminated in the development of "artificial pancreas" devices (APDs) that can autonomously deliver insulin in response to real-time glucose measurements. However, the current generation of APDs rely heavily on model predictive control algorithms that deliver insulin based solely upon current glucose trends. In these systems, insulin onset and duration of action is derived from generalized patient data. However, patients have diverse responses to insulin due to differences in insulin sensitivities, insulin absorption rates from injections sites, and insulin clearance rates. If the timing of insulin action in an individual patient deviates from the generalized data given to the algorithm, there is a risk of incorrectly estimating insulin doses. Insulin can be life-threatening when not dosed correctly, and therefore it is imperative that patients have a better understanding of their personal response to insulin. Individual patient insulin tracking is crucial to understand insulin absorption profiles and has the potential to improve APDs and diabetes management. Unfortunately, with current technologies, understanding individualized insulin kinetics is laborious and most treatment decisions continue to be made with a combination of representative population data combined with trial and error.

Beyond insulin, there is a need in the art for devices and methods which enable continuous tracking of multiple disease-related biomarkers' fluctuating concentration levels directly from whole blood in live subjects. The conventional bench-top enzyme-linked immunosorbent assay (ELISA) process includes several hours of incubation, averting rapid and fast measurement of the biomarker levels. For measuring biomarkers in vivo, current tools are primitive in that they lack the necessary specificity, detection sensitivity, and temporal resolution. There is therefore an urgent need to establish a new, in vivo measurement technology capable of multi-analyte detection.

SUMMARY OF THE INVENTION

One embodiment of the present disclosure provides a method for determining a continuous, real-time concentration of one or more molecules in a subject, comprising: (a) continuously flowing a biological fluid from the subject to a microfluidic device; (b) administering a capture solution comprising an affinity agent and optionally a detection agent, at one or more time periods during step (a) to the microfluidic device; (c) mixing the biological fluid and the capture solution under conditions that allow the one or more molecules in the biological fluid to contact and bind the affinity agent to form a complex, and optionally to allow the detection agent to bind to the one or more molecules in the biological fluid that have been bound to the affinity agent; (d) optionally depleting biological fluid components that are not bound by the affinity agent in step (c); (e) detecting the presence of the complex by detecting a detection signal from each of the one or more molecules bound by the affinity agent and optionally the detection agent; and (f) determining the concentration of the one or more molecules.

In another embodiment, the aforementioned method is provided wherein the concentration of at least 2 molecules is determined. In other embodiments, the concentration of at least 3, 4, 5, 6, 7, 8, 9, or 10 molecules is determined.

In various embodiments, an aforementioned method is provided wherein the molecule is selected from the group consisting of: a small molecule, a protein, and a carbohydrate. In some embodiments, the small molecule is selected from the group consisting of a drug, a metabolite, a neurotransmitter and a neurochemical. In some embodiments, the metabolite is an endogenous metabolite derived from one or more alcohols, one or more amino acid, one or more nucleic acids, one or more organic acids, one or more antioxidants and/or one or more vitamins. In still other embodiments, the metabolite is a metabolite of a therapeutic agent, wherein the therapeutic agent is a drug. In various embodiments, the drug is selected from the group consisting of: a chemotherapeutic agent, an antibiotic, a vaccine component and a therapeutic polypeptide. In related embodiments, the antibiotic is selected from the group consisting of doxorubicin, kanamycin, tobramycin, and gentamicin.

In still other embodiments of the present disclosure, an aforementioned method is provided wherein the protein is selected from the group consisting of an antigen, a signaling molecule, a hormone, and a cytokine. In some embodiments, the hormone is selected from the group consisting of: insulin, glucagon, cortisol, oxytocin, and vasopressin. In other embodiments, the cytokine is selected from the group consisting of: a chemokine, an interferon, an interleukin, a lymphokine, and a tumor necrosis factor. In various embodiments, the interleukin is interleukin-1 (IL-1), interleukin-6 (IL-6), interleukin-12 (IL-12) and/or interleukin-10 (IL-10). In still other embodiments, the molecule is a cytokine such as IL-1, IL-2, IL-3, IL-4, IL-5, IL-6, IL-8 family, IL-10, IL-12, IFN-gamma, TGF-beta, GM-CSF, and/or TNF-alpha. In still other embodiments, the protein is selected from the group consisting of high-mobility group box-1 (HMGB1), C-reactive protein (CRP) and tumor necrosis factor-alpha (TNF-$\alpha$).]

In various other embodiments, an aforementioned method is provided wherein the carbohydrate is a monosaccharide or a polysaccharide. In one embodiment, the monosaccharide is glucose.

In still other embodiments, an aforementioned method is provided wherein the protein is selected from the group consisting of: a troponin protein or troponin complex.

In yet other embodiments, an aforementioned method is provided wherein the neurochemical is selected from the group consisting of: neuropeptide Y, neurotensin, Substance P, dopamine, serotonin, epinephrine, and acetylcholine.

Various reagents are used with the described methods herein. In some embodiments, an aforementioned method is provided wherein the affinity agent comprises an antibody or aptamer micro-bead. In some embodiments, the affinity agent comprises a microbead (e.g., wherein the aptamer and antibody are the affinity reagents and are immobilized on the surface of the microbeads). In another embodiment, the aptamer is conjugated to a detection agent (e.g., a reporter). In some embodiments, the antibody is conjugated to the micro-bead to allow binding of the antibody to the one or more molecules in the biological fluid, and wherein a detection agent is also capable of binding the one or more molecules in the biological fluid. In one embodiment, the detection agent comprises a fluorophore.

In still other embodiments, an aforementioned method is provided wherein the capture solution comprises at least 2 different affinity agents capable of forming a complex with at least 2 different molecules, and further comprises at least 2 different detection agents capable of forming a complex with the at least different molecules in a complex with the at least 2 different affinity agents. In various embodiments, the micro-bead is between 15-30 μm in diameter. In one embodiment, the micro-bead is 15 μm in diameter.

In yet other embodiments, an aforementioned method is provided wherein the biological fluid is selected from the group consisting of, whole blood, serum, plasma, interstitial fluid, saliva, urine, and cerebrospinal fluid. In one embodiment, the subject is a human.

In various embodiments, an aforementioned method is provided wherein the microfluidic device comprises at least one lane, wherein each lane comprises a module for mixing as set out in step (c), optionally a module for depleting as set out in step (d), and a module for detection as set out in step (e). In one embodiment, the mixing module comprises a lane set out in a serpentine configuration. In one embodiment, the mixing of the biological fluid and the capture solution occurs in less than 1 minute.

In yet other embodiments, an aforementioned method is provided wherein the depletion module comprises an arrangement of posts to deplete biological fluid components that are not bound by the affinity agent. In one embodiment, the depletion of biological fluid components that are not bound by the affinity agent occurs in less than 30 seconds.

In still other embodiments, an aforementioned method is provided wherein the detection module is operably associated with an image-capturing device capable of detecting the presence of the complex. In one embodiment, the image-capturing device is a camera. In one embodiment, the camera is a sCMOS camera.

In some embodiments, an aforementioned method is provided wherein concentration of the one or more molecules is determined by measuring fluorescence intensity.

In still other embodiments, an aforementioned method is provided wherein the microfluidic device is operably attached to the surface of the subject.

Methods of treatment are also contemplated by the present disclosure. In one embodiment, a method of treating a disease or disorder in a subject is provided, said method comprising an aforementioned method, and further comprising continuously or intermittently administering a therapeutic agent based on the determined concentration of the one or more molecules, wherein the one or more molecules are associated with the disease or disorder, thereby treating said subject.

In still other embodiments of the present disclosure, an aforementioned method is provided further comprising the step of amplifying the detection signal, wherein said amplifying comprises administering a composition comprising amplification agents. In one embodiment, the amplification agents comprise (1) two antibodies capable of binding to the same molecule, wherein each antibody has been conjugated with an oligonucleotide that are capable of at least partially hybridizing, and (2) two oligonucleotide molecules that have been conjugated with a detection label; wherein said amplification agents are capable of undergoing a hybridization chain reaction. In still another embodiment, the amplifying allows detection of one or more molecules that are present in the sample at a concentration of approximately in the range of femtomolar (fM, i.e., $10^{-15}$ moles per liter) to picomolar (pM, i.e., $10^{-12}$ moles per liter). In still other embodiments, the amplifying occurs continuously.

In yet another embodiment, an aforementioned method is provided by the present disclosure, wherein the detection agent is administered after administration of the affinity agent. In another embodiment, the detection agent is administered after administration of the affinity agent, wherein the amplification agents are administered after administration of the detection agent.

In still another embodiment, the present disclosure provides an aforementioned method wherein the sample is administered to the microfluidic device using a syringe pump. In yet another embodiment, the present disclosure provides an aforementioned method wherein said microbead is magnetic and said depletion comprises flowing the sample and capture solution and optionally the detection agent of step (b) over a magnetized channel or module in the microfluidic device.

In another embodiment, a method of determining a continuous, real-time concentration of a molecule in a subject is provided, comprising: (a) continuously flowing whole blood from the subject to a microfluidic device; (b) administering a capture solution comprising (i) a micro-bead conjugated to an antibody that is capable of binding to the molecule at one or more time periods during step (a) to the microfluidic device, and (ii) a detection agent comprising an antibody conjugated to a fluorophore and that is capable of binding to the molecule that is bound by the micro-bead-conjugated antibody; (c) mixing the whole blood and the capture solution under conditions that allow the molecule in the whole blood to contact and bind the affinity agent to form a complex; (d) depleting biological fluid components that are not bound by the affinity agent in step (c); (e) detecting the presence of the complex; and (f) determining the concentration of the molecule.

In still another embodiment, a method of determining a continuous, real-time concentration of insulin in a subject is provided, comprising: (a) continuously flowing whole blood from the subject to a microfluidic device; (b) administering a capture solution comprising (i) a micro-bead conjugated to an antibody that is capable of binding to insulin at one or more time periods during step (a) to the microfluidic device, and (ii) a detection agent comprising an antibody conjugated to a fluorophore and that is capable of binding to insulin that is bound by the micro-bead-conjugated antibody; (c) mixing the whole blood and the capture solution under conditions that allow the insulin in the whole blood to contact and bind the antibody conjugated to the micro-bead and the detection agent to form a complex; (d) depleting biological fluid components that are not bound by the antibody conjugated to the micro-bead in step (c); (e) detecting the presence of the complex; and (f) determining the concentration of the insulin.

In yet another embodiment, a method of determining a continuous, real-time concentration of glucose in a subject is provided, comprising: (a) continuously flowing whole blood from the subject to a microfluidic device; (b) administering a capture solution comprising (i) a micro-bead conjugated to an aptamer that is capable of binding to glucose at one or more time periods during step (a) to the microfluidic device; (c) mixing the whole blood and the capture solution under conditions that allow the glucose in the whole blood to contact and bind the aptamer to form a complex; (d) depleting biological fluid components that are not bound by the aptamer in step (c); (e) detecting the presence of the complex; and (f) determining the concentration of the glucose.

BRIEF DESCRIPTION OF THE DRAWINGS

FIG. 3B shows insulin probe validation: microbeads functionalized with the capture antibodies were incubated with different concentrations of insulin and the detection antibodies labeled with PE fluorophore. After an hour incubation, beads were washed three times and monitored under the imaging setup with green laser excitation to excite PE fluorophore (left) and the fluorescence signal intensity was measured for different concentrations (right). For each concentration in A and B, at least 10 beads were measured, and the error bars show SD among the beads. FIG. 3C shows CGIM was used to measure the endogenous insulin secreted from human islet samples through an in-vitro secretion assay where insulin secretion was measured after a glucose challenge. The readout was compared to the conventional ELISA assay measurements. The experiment was performed three times with human islets obtained from three different donors.

FIGS. 4A-4B show the continuous, in-vitro monitoring of varying concentrations of glucose and insulin directly in whole blood. Continuous, real-time measurement of glucose (FIG. 4A) and insulin (FIG. 4B) in human whole blood (dots) relative to actual concentrations [over the course of 30 mins. Insets show the standard curves relating fluorescence signal intensity to glucose or insulin concentrations. Data are the individual beads readout where, for each concentration, at least 200 beads were measured. Different concentrations of glucose and insulin were simultaneously spiked in whole human blood samples and injected into the CGIM for continuous monitoring ([Glucose, insulin]: [15 mM, 1.6 nM]; [5 mM, 0.4 nM]; [10 mM, 0.8 nM]; [8 mM, 0.2 nM]; [20 mM, 1 nM]). For each concentration, measurements were performed for 2 mins and between changing the sample, buffered solution was injected to the device for 4 mins. The fluorescence signal intensity from the blank sample (sample not spiked with insulin or glucose) was measured to consider the endogenous insulin and glucose. For insulin measurements, the fluorescence signal intensity from the blank sample was subtracted from the measured signal at each concentration. For glucose measurements, the endogenous glucose was measured using the conventional glucose meter and subtracted as baseline before calculating the spiked concentrations.

FIGS. 5A-5F shows continuous, real-time measurements of glucose and insulin in a diabetic rat. RT-ELISA measurement of in vivo glucose (FIG. 5A, C, E) and insulin (FIG. 5B, D, F) concentrations over 30-50 mins in three different rats. Diabetic rats were injected subcutaneously with a single bolus of Humulin R at t=0 (FIG. 5A-D) or two boluses at t=0 and 20 min (FIG. 5E, F). Each blue dot shows the median RT-ELISA readout of individual bead (~150 beads) measurements over 30 sec. For comparison, we collected blood samples from the tail vein every 5 mins, and measured glucose and insulin levels via handheld glucose meter and conventional ELISA, respectively (squares). These results correlated closely, and highlight the inter-individual variability in insulin response.

FIGS. 7A-7C show a comparison of different insulin formulation pharmacokinetics. Diabetic rats were injected with either Humulin R or Humulin N and RTCM was applied to track glucose (FIGS. 7A and B) insulin (FIG. 7C) levels. The RTCM measurements (dots) evidently show the different kinetics in two types of insulin. In FIG. 7B, for the first 35 mins, the blood glucose was greater than the detection limit of the handheld glucose monitor and could not be measured.

FIG. 9 shows the amplification assay results. Benchtop-incubated bead-based binding assays comparing fluorescent signal of HCR-amplified 3-binder sandwich assay with a similar non-amplified assay with fluorophore-labeled detection antibodies. These assays were conducted with one bead wash immediately before imaging. Results show a significant increase in fluorescent signal. While the un-amplified assay enables target detection up to approximately one order of magnitude below the functional KD of the assay, the HCR amplification extends the useful detection range of the assay to over two orders of magnitude below the functional KD of the assay. A finer resolution of target concentrations is observed over a wider range of target concentrations.

FIG. 10 shows the detection probes in detail.

DETAILED DESCRIPTION

Figure 1:
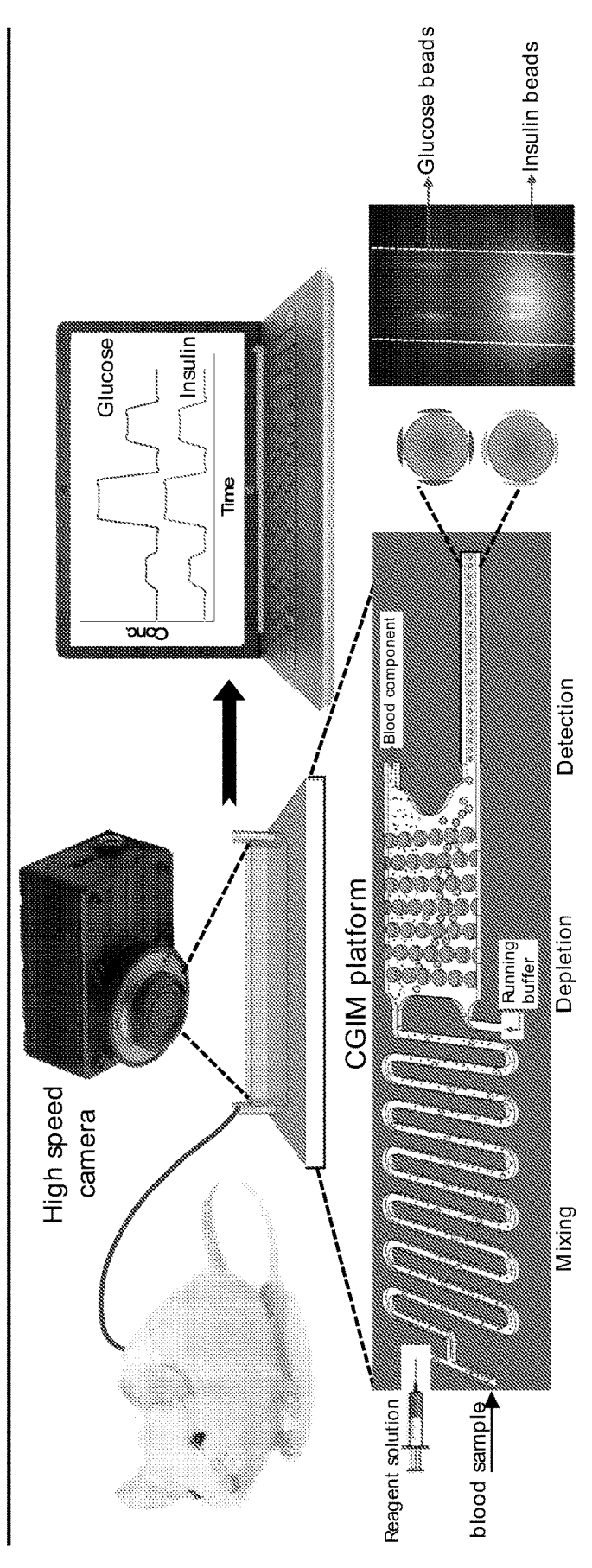
FIG. 1 is a diagram depicting various embodiments of the real-time, continuous monitoring ("RTCM") methods and device provided by the present disclosure. The continuous glucose and insulin monitoring ("CGIM") device measures transient changes in glucose and insulin levels.

The present disclosure addresses the aforementioned unmet need by providing methods and materials for real-time, continuous monitoring ("RTCM") of molecules. One example of a RTCM according to one embodiment is a continuous glucose and insulin monitoring ("CGIM") device that measures transient changes in glucose and insulin levels as described herein.

The present disclosure provides a biosensor to constantly process samples and integrate several steps, such as purification, incubation, and washing. As described herein, the sensor exhibits sufficient sensitivity, specificity and dynamic range in measuring low abundance molecules directly in whole blood resolves temporal fluctuations over short timescale (minutes). As further described herein, the present disclosure provides a system to perform multiplexed measurements of more than one molecule simultaneously.

The present disclosure provides a universal platform that uses a molecular probe (e.g., a micro-bead conjugated with an antibody capable of binding to a target molecule) and, by changing the probes, it can be applied for in-vivo, multiplexed, and continuous measurement of any target molecule of interest. In exemplary embodiments, the real-time monitoring of glucose and insulin is demonstrated. Real-time monitoring of glucose and insulin simultaneously has potential to add additional information in a closed-loop system and allow for improved autonomous control. In the clinic, real-time glucose and insulin measurements would enable clinicians to gain a better understanding of individualized insulin kinetics and the impact it has on insulin action.

Definitions

As used herein, the term "molecule" and "target molecule" refers to a moiety such as a chemical compound or biological molecule and therefore includes biomolecules, biomarkers, drugs, analytes, metabolites, hormones, neurochemicals/neurotransmitters, cytokines, antigens, and the like.

The phrase "continuous, real-time" as used herein refers to monitoring the presence of a molecule or determining the concentration of a molecule using a continuous supply and flow of biological fluid from a live subject. It will be readily apparent to those of skill in the art that "continuous" and "real-time" is different than conventional techniques which may require pausing a process in order to collect and examine samples. In various embodiments of the present disclosure, multiple molecules are directly detected and/or quantified using a microfluidic device (in association with a device capable of optical measurements) without collection of a sample.

As used herein, the terms "determining," "measuring," "assessing," and "assaying" are used interchangeably and include both quantitative and qualitative determinations unless the context clearly indicates otherwise.

The term "capture solution" or "reagent solution" as used herein refers to a composition comprising an affinity agent and which is administered directly to a microfluidic device described herein to allow contact and mixing with a biological fluid.

As used herein, the term "affinity agent" refers to a binding agent, such as an antibody or an aptamer, or a group of binding agents capable of binding one or more target molecules and which report a detectable signal indicative of a specific binding interaction with a target molecule, e.g., a target analyte or biomolecule. In one embodiment, an affinity agent may comprise a "capture agent" and a "reporter agent." As used herein, exemplary affinity agents include, but are not limited to, antibodies or aptamer that are conjugated to micro-beads. In this example, the antibody is the capture agent. ELISA techniques, including direct ELISA, indirect ELISA, sandwich ELISA and competitive ELISA are contemplated herein. The terms "reporter agent," "label" and "detectable label" may be used interchangeably herein to refer to a molecule capable of detection, including, but not limited to, radioactive isotopes; redox reporters; luminescers, e.g., bioluminescers, chemiluminescers, electroluminescers, and photoluminescers, e.g., fluorescers; chromophores; enzymes; enzyme substrates; enzyme cofactors; enzyme inhibitors; dyes; metal ions; metal sols; ligands (e.g., biotin, avidin, strepavidin or haptens) and the like. Exemplary detectable moieties suitable for use as detectable labels include affinity tags and fluorescent reporter. The term "affinity tag" is used herein to denote a peptide segment that can be attached to a target that can be detected using a molecule that binds the affinity tag and provides a detectable signal (e.g., a fluorescent compound or protein). In principal, any peptide or protein for which an antibody or other specific binding agent is available can be used as an affinity tag. Exemplary uses of the aforementioned labels and tags include the enzyme-linked immunosorbent assay (ELISA) and related techniques as described herein.

As used herein the term "aptamer" or "aptamer sequence" refers to a nucleic acid having a specific binding affinity for a target, e.g., a target molecule, wherein such target is other than a polynucleotide that binds to the aptamer or aptamer sequence through a mechanism which predominantly depends on Watson/Crick base pairing. As described herein, an aptamer can be used in accordance with various embodiments of the disclosure where, for example, an antibody is not available for detection of a (small) biomolecule (e.g., glucose).

The term "sequence" as used, for example, in the context of an aptamer sequence, a nucleic acid sequence or an amino acid sequence may refer to the primary structure, e.g., the order of monomeric subunits, e.g., nucleotides or amino acids, and/or to the molecule having the primary structure.

The terms "antibody" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins including an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. Also encompassed by the terms are Fab', Fv, F(ab').sub.2, and other antibody fragments that retain specific binding to antigen. Antibodies may exist in a variety of other forms including, for example, Fv, Fab, and (Fab').sub.2, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., Immunology, Benjamin, N.Y., 2nd ed. (1984), and Hunkapiller and Hood, Nature, 323, 15-16 (1986).

The terms "specific binding," "specifically bind," and the like, refer to the ability of a first binding molecule or moiety to preferentially bind (covalently or non-covalently) to a second binding molecule or moiety relative to other molecules or moieties in a reaction mixture.

As used interchangeably herein, the terms "active agent", "pharmacologically active agent" and "beneficial agent" refer to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a conformation switching probe" includes a plurality of such conformation switching probes and reference to "the microfluidic device" includes reference to one or more microfluidic devices and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

Molecules and Biomarkers

The present disclosure provides a universal platform that uses a molecular probe and, by changing the probes, it can be applied for in-vivo, multiplexed, and continuous measurement of any target molecule of interest. In various embodiments the systems, devices and methods described herein are useful for measuring, for example determining the presence of or determining the concentration of, proteins, small molecules and other biomolecules and can be implemented in the biomedical research, such as infectious diseases, neuroscience, immunology, cancer, and others, as well as the broader goal of providing continuous and personalized monitoring of drugs and the body's reaction to drugs, including drug metabolites. This disclosure also permits the continuous monitoring of disease-related agents in emergency rooms for the early diagnosis of a variety of high-mortality rate diseases, such as sepsis, a systemic response to infection which is the most expensive condition to treat in the healthcare system; and myocardial infarction, the second leading cause of death and the leading cause of hospitalization worldwide.

In recent years, many lab-on-a-chip (LOC) devices have been developed with the aim of simplifying and improving the performance of immunoassays including ELISA. These technologies were able to reduce the operation time from several hours in benchtop ELISA assay to 20-30 minutes. However, these tools functioned in stationary or "near" real-time mode and measured the biomarker levels one at a time. For example, a bead-based immunoassay integrated into a microfluidic device was developed for rapid quantitation of insulin (Cohen, N. et al. Microchim. Acta 184, 835-841 (2017) & Kahanovitz, L. et al., J. Diabetes Science and Technology, 10(3):689-696, 2016). Mixing in two serpentine channels of a microfluidic device was employed for the formation of sandwich ELISA and the fluorescence intensity was measured in flow. The method was applied to near real-time monitoring of insulin in serum sample. A fasting T1D patient was injected with insulin and the measurement was performed at time 0, 1 hr, 2 hr, 3 hr and 3.5 hr after the injection.

In another example, an ELISA-LOC device was prepared which integrated a microfluidic system into a miniature ninety-six sample plate (Sun, S., et al., Lab Chip 10, 2093-2100 (2010)). The device demonstrated the advantage of integrating the washing step directly into an ELISA plate. In another example, a disc-based, micro-bead sandwich ELISA system was developed to detect infectious disease biomarkers from whole blood (Lee, B. S. et al. Lab Chip 9, 1548-1555 (2009)). In another example, an integrated point-of-care platform was developed which converts the molecular recognition signal into a distance readout for visual analysis. This integrated ELISA-Chip allows the quantitation of disease biomarkers within 2 h (Liu, D. et al., Biosens. Bioelectron. 96, 332-338 (2017)). In another example, a mobile chip (mChip) integrating microfluidics and nanoparticles was developed to achieve POC diagnosis of clinically relevant infectious diseases (Umviligihozo, G. et al. Nat. Med. 17, 1015-1019 (2011)). The system performs the procedures within 20 min and simultaneously diagnose HIV and syphilis with high sensitivity using absorbance measurement.

An electrochemical aptamer-based (E-AB) sensors (Arroyo-currás, et al., PNAS, 114(4):645-650, 2016) were demonstrated to support continuous, real-time, multihour measurements when emplaced directly in the circulatory systems of living animals. The E-AB sensors were used to perform the multihour, real-time measurement of four drugs in the bloodstream of an awake, ambulatory rats, achieving precise molecular measurements at clinically relevant detection limits and 3 s temporal resolution. This suggests that the approach could provide an important window into the study of physiology and pharmacokinetics. However, the E-AB sensors were applied for continuous tracking of drugs, it is still limited to high abundance biomolecules and cannot perform the multiple measurements simultaneously.

The present disclosure provides devices, methods and systems for molecule detection and/or monitoring, e.g., the continuous, real-time monitoring of in-vivo molecule concentrations. Ferguson et al. developed a real-time biosensor capable of continuously tracking of circulating drugs in living subjects. The microfluidic electrochemical detector for in vivo continuous monitoring (MEDIC) device has an aptamer probe at the heart of the sensor, labeled with a redox reporter and immobilized onto an electrode within a microfabricated device. Upon binding to its target, the aptamer undergoes a conformational change and produces a change in faradaic current that can be directly measured using standard voltammetry instruments. The MEDIC device was employed to quantitative, real-time detection of fluctuating concentrations of doxorubicin (DOX), a widely-used chemotherapy agent, in flowing human whole blood in-vitro as well as in-vivo in live, anesthetized rats (Ferguson et al., Sci. Transl. Med., 5(213), 2013). Although MEDIC demonstrates the continuous monitoring, it only enables the measurement of high abundance biomolecules such as DOX and cannot be applied to monitor clinically relevant, low abundance biomolecules. Moreover, it is limited to single biomarker measurement.

Chemical compounds such as drugs and drug metabolites, antibiotics, carbohydrates and analytes are each contemplated by the present disclosure. Likewise, in various embodiments, biological molecules ("biomolecules") including biomarkers, proteins and peptides, hormones, neurochemicals ("neurotransmitters"), cytokines, antigens, and antibodies are provided by the present disclosure. By way of example, the present disclosure provides methods and devices and systems for the continuous, real-time monitoring of neurochemicals, such as neuropeptide Y, neurotensin, Substance P, dopamine, serotonin, epinephrine, and acetylcholine. Drugs that are particularly and traditionally hard to dose, such as insulin, glucagon, cortisol, oxytocin, and vasopressin, doxorubicin, kanamycin, tobramycin, and gentamicin are also contemplated herein. Indicators of diseases, disorders, or physiological stress such as troponin (heart attacks), cytokines (sepsis), and glucose (diabetes) are provided. In some embodiments, the molecule is one or more of high-mobility group box-1 (HMGB1), C-reactive protein (CRP) and tumor necrosis factor-alpha (TNF-$\alpha$), glucose, troponin protein or troponin complex, IL-1, IL-2, IL-3, IL-4, IL-5, IL-6, IL-8 family, IL-10, IL-12, IFN-gamma, TGF-beta, GM-CSF, and/or TNF-alpha.

The methods, devices and systems of the present disclosure can support multiple affinity agents, e.g., located on or in multiple devices or lanes within a single microfluidic device, to examine a range of molecules. This could include, e.g., a drug, and its metabolites (such as chemotherapeutic methotrexate, and its metabolite 4-amino-4-deoxy-N-methylpteroic) or biomarkers that are indicative of the disease (such as Carcinoembryonic Antigen for cancer) or the impact of the treatment (such a creatinine indicating kidney function).

The devices, methods and systems of the present disclosure facilitate continuous monitoring of molecule levels or concentration in real time, and may be used in connection with known medication delivery devices to provide appropriate drug delivery systems, including open- and closed-loop systems. Accordingly, in some embodiments the devices, methods and systems of the present disclosure may facilitate direct control of in vivo concentrations of therapeutics in response to ongoing metabolic changes in a subject, thereby allowing for dose optimization based on individual subject response.

As described herein, the present disclosure provides materials and methods for monitoring, optionally determining the concentration of, molecules in real-time and from a continuous flow of biological fluid from a patient.

As exemplary embodiments of the present disclosure, continuous measurement of physiological concentrations of glucose and insulin in human whole blood is provided as described herein. This is the first real-time biosensor that achieves continuous measurement of rare and low abundance molecules like insulin directly in whole blood samples. Previously reported technologies for real-time molecular monitoring have only enabled the measurement of high abundance molecules, such as drugs (Ferguson et al., Sci. Transl. Med., 5(213), 2013), lactate (Baker & Gough, Anal. Chem., 67:1536 (1995), glucose (Hovorka, Diabetes Medicine, 23(1), 1-12, 2006), and high abundance neuromodulator (Nakatsuka et al., Science, 2019). Here, experiments in diabetic rats demonstrate that the RTCM or CGIM technique allows for simultaneous tracking of multiple biomarkers in-vivo, and it is effective at observing different insulin formulation pharmacokinetics in individual rats.

Insulin is one of the most important therapeutic molecules, with over 50 million diabetes patients worldwide requiring insulin replacement therapy (WHO. Diabetes: Key Facts. World Health Organization. https://www.who.int/news-room/fact-sheets/detail/diabetes (2018)). The present disclosure enables personalized insulin monitoring in individual patients, which is critical to improve our understanding of variable insulin action in patients and would enable improved diabetes management. While patients work with endocrinologists to monitor glucose levels and to determine insulin dosing to remain in their target glucose range, monitoring of insulin levels or absorption rates is rarely considered. Insulin absorption can vary with temperature or exercise and it is important for patients to understand how this variation is related to the glucose response. If clinicians are able to determine patient insulin kinetics and subsequent glucose response, the insulin profiles in APD devices can be customized to improve glucose control. Monitoring insulin is especially important in preventing post-prandial hypoglycemia, where the long duration of insulin action can result in unexpected insulin on board long after mealtimes. In the future, insulin measurements attained from RTCM could be directly incorporated into APDs and could enable the development of next-generation APDs that will be more robust and safer for diabetes patients.

Methods of Determining Continuous, Real-Time Concentration

Existing biosensor technology for the continuous measurement of specific biomolecules in vivo is currently limited to a handful of molecules, such as glucose, lactate, and oxygen. These sensors rely on unique biochemical features of the biomarker to achieve real-time detection, and thus cannot be generalized to other molecules. For measuring other biomarkers in vivo, current tools are primitive in that they lack the necessary specificity, detection sensitivity, and temporal resolution. There is therefore an urgent need to establish a new in vivo measurement technology and methods capable of multi-analyte detection.

One embodiment of the present disclosure provides a biosensor (Real-Time enzyme-linked immunosorbent assay or RT-ELISA) which enables continuous tracking of multiple disease-related biomarkers' fluctuating concentration levels directly from whole blood in live subjects. ELISA has been the gold standard and the most commonly used assay in clinical diagnostics to quantify small concentrations of antibody or antigen in the biological samples. The conventional bench-top ELISA process includes several hours of incubation, averting rapid and fast measurement of the biomarker levels.

The RT-ELISA biosensor is a generalizable platform that can be readily applied to continuous in vivo monitoring and detection of clinically relevant target molecules in real-time. Since a single biomarker cannot always diagnose disease with high confidence, the sensors, devices, systems and methods disclosed herein are capable of performing multiplexed measurements for multiple biomarkers simultaneously. This provides, e.g., physicians, valuable information about patients' health status and thereby yielding more effective treatments for a broad range of medical conditions.

The disclosed devices and systems facilitate a variety of detection and/or monitoring methods, e.g., detection and/or monitoring, e.g., in vivo detection and/or monitoring, of whole blood or other biological fluids for a target molecule of interest. As described herein, the disclosed devices and systems are used to determine the concentration of 1, 2, 3, 4, 5, 6, 7, 8, 9, 10 or more target molecules.

In some embodiments, 10, 20, 30, 40, 50, 60, 70, 80, 90 or 100 or more molecules may be detected (e.g., using xMAP®, Luminex Corp.).

In some embodiments, micro-beads (bead size>15 μm) are used to capture biomolecules in whole blood. As the blood enters the associated microfluidic device, reagent solution (i.e., capture solution)—micro-beads functionalized with capture antibodies and fluorescence tags—is injected through a reagent inlet and efficiently mixed to form a sandwich ELISA. The conventional bench-top ELISA process requires a long incubation time (hours) because of the inefficient mass transport of the analyte to the surface of microtiter plates. In the RT-ELISA device of the present disclosure, a chaotic mixer dramatically enhances the rate of molecular diffusion and reduces the incubation time to less than a minute (Thompson, J. & Bau, H., J Chromatogr B Anal. Technol Biomed Life Sci 2, 1-26 (2011)). Subsequently, the biomolecules captured by the antibody coated micro-beads are separated from blood cells using a depletion module as described herein, which employs deterministic lateral displacement (DLD) sorting. DLD is a hydrodynamic method that enables the separation of particles purely based on size in a continuous manner (McGrath, J., et al., Lab Chip 14, 4139-4158 (2014)). Micro-beads are next flowed into a detection module and their fluorescence intensity is continuously measured using, in some embodiments, a high speed, CCD camera. The fast frame rate and high sensitivity of the camera enables the continuous tracking of individual micro-beads passing through the detection window, and enables quantitative detection of biomolecules in real-time.

Accordingly, in some embodiments, the present disclosure provides methods of determining an in vivo concentration of a target molecule. In some embodiments, such a method includes a method of determining a continuous, real-time concentration of one or more molecules in a subject, comprising: (a) continuously flowing a biological fluid from the subject to a microfluidic device; (b) administering a capture solution comprising an affinity agent at one or more time periods during step (a) to the microfluidic device; (c) mixing the biological fluid and the capture solution under conditions that allow the one or more molecules in the biological fluid to contact and bind the affinity agent to form a complex; (d) optionally depleting biological fluid components that are not bound by the affinity agent in step (c); (e) detecting the presence of the complex; and (f) determining the concentration of the one or more molecules.

In various embodiments, the concentration of at least 3, 4, 5, 6, 7, 8, 9, or 10 molecules is determined. The capture solution may be administered to the microfluidic device simultaneously with the biological fluid, or at one or more times after the biological fluid begins flowing from the subject to the microfluidic device.

In various embodiments, a method is provided as described herein wherein the affinity agent includes a micro-bead. Micro-beads suitable for the materials, e.g., microfluidic devices, and methods described herein are known in the art. Micro-beads can be approximately—15, 20, 25, or 30 μm in diameter. In one embodiment, the micro-bead is 15 μm in diameter.

In some embodiments, one or multiple antibodies or aptamers are conjugated to the micro-beads.

In some embodiments, the antibody or aptamer is conjugated to a detection moiety. In one embodiment, the detection moiety is a fluorophore.

As described herein, the capture solution may, in various embodiments, comprise at least 2 different affinity agents capable of forming a complex with at least 2 different target molecules. By way of example, 2, 3, 4, 5, 6, 7, 8, 9, 10 or more different affinity agents capable of forming a complex with at least 2 different molecules are provided.

The present disclosure provides for continuous flow of a biological fluid from a subject. The biological fluid can be, in various embodiments, whole blood, serum, plasma, interstitial fluid, saliva, urine, or cerebrospinal fluid.

Human, animal, primate and rodents are all contemplated according to the present disclosure. In one embodiment, the subject is a human suffering from a disease or disorder. By way of example, the human subject is a diabetic or is symptomatic of a heart attack or sepsis or patients that undergo dialysis treatment.

In still other embodiments of the disclosure, a method of treating a disease or disorder in a subject is provided, said method comprising the methods described herein and further comprising continuously or intermittently administering a therapeutic agent based on the determined concentration of the one or more molecules, wherein the one or molecules are associated with the disease or disorder, thereby treating said subject.

Additional methods are also contemplated. For example, a method of continuously monitoring the presence and/or concentration of a disease-related agent in a patient is provided, said method comprising the methods described herein, wherein the molecule is a disease-related agent, such as an antigen or insulin.

In another embodiment, a method of continuously monitoring the presence and/or concentration of a drug that has been administered to a subject is provided, said method comprising the methods described herein, wherein the molecule is the administered drug, such as a therapeutic antibody, a chemotherapeutic, or insulin.

In another embodiment, a method of modulating an in vivo concentration of one or more molecules is provided, said method comprising the methods described herein, and further comprising continuously or intermittently administering a molecule or a pharmacologically active agent capable of modulating the presence of said molecule, based on the determined presence or concentration of the one or more molecules, wherein the in vivo concentration of the one or more biomarkers is modulated. Additionally, in another embodiment, a method is provided wherein the continuous or intermittent administration of the molecule or therapeutic agent is carried out using a feedback loop in communication with the microfluidic device.

As described herein, detection of the target molecule or target molecules may be carried out using an ELISA. The conventional ELISA is a plate-based assay technique designed for detecting and quantifying substances such as peptides, proteins, antibodies and hormones. Other names, such as enzyme immunoassay (EIA), are also used to describe the same technology.

In some embodiments, in the detection module of a device described herein, the complex bead-target flow into a detection window and their fluorescence intensity is continuously measured using a high-speed camera under spatially-multiplexed two-color laser illumination. Incoming beads are illuminated by the red laser first, which interrogates the Cy5 fluorescence intensity that indicates real-time first target molecule concentrations, before being illuminated by a green laser which interrogates the PE fluorescence intensity that indicates second target molecule concentrations. The exposure time of 50 ms can be used and the images are acquired every 100 ms. In some embodiments, 5 beads per second are observed passing through the detection window. The fast frame rate and high sensitivity of camera allow continuously tracking individual microbeads and enable quantitative detection of analytes in real-time.

By monitoring the levels of specific molecules, e.g., drugs, metabolites, or biomarkers using the disclosed methods, devices and systems, it is possible to inform adaptive therapies through feedback control (Mage et al., Nat. Biomed. Eng., 1(5):1-10, 2017)). This allows for adjustment of therapeutic administration for a given patient based on phenotypic and metabolic state. For example, the concentration of a specific drug could be controlled directly by measuring its concentration in circulation or the concentration of a specific drug could be controlled by measuring the concentration of related metabolites, or linked biomarkers.

By facilitating real time monitoring of in vivo molecule concentrations, including plasma concentrations, the disclosed methods, devices and systems facilitate the determination of a variety pharmacokinetic parameters for pharmacologically active agents. For example, pharmacokinetic parameters such as peak plasma concentration ($C_{max}$), minimum plasma concentration ($C_{min}$), steady state concentration ($C_{ss}$), time to reach $C_{max}$ ($T_{max}$), plasma half-life ($T_{1/2}$), area under curve (AUC), volume of distribution (Vd), bioavailability and clearance may be readily determined using the methods, devices and systems of the present disclosure.

As described herein, other embodiments of the present disclosure include (1) continuous signal amplification via, for example, Hybridization Chain Reaction (HCR) to allow for detection of low abundance molecules (for example, proteins), (2) staged incubation in the microfluidic devices described herein to optimize assay performance, and (3) device configurations for both an intermittent and continuous mode.

Microfluidic Devices

The present disclosure provides microfluidic devices which find use, for example, in the disclosed methods and systems. In some embodiments, a microfluidic device according to the present disclosure comprises at least one lane, wherein each lane comprises a module for mixing as set out in step (c), optionally a module for depleting as set out in step (d), and a module for detection as set out in step (e). In various embodiments, the microfluidic device comprises, 1, 2, 3, 4, 5, 6, 7, 8, 9, 10 or lanes.

In one embodiment, the mixing module of the microfluidic device comprises a lane set out in a serpentine configuration, thereby enabling chaotic mixing. In some embodiments, the mixing module allows one or more target biomolecules to come into contact with an antibody conjugated to a micro-bead and fluorescently labeled using detection antibodies. To achieve, rapid and continuous mixing of reagents within microfluidic channels, serpentine channels with optimized length and embedded herringbone structures inside the channel is provided (Marschewski, J. et al. Lab Chip 15, 1923-1933 (2015)).

In various embodiments, the mixing of the biological fluid and the capture solution occurs in less than 1, 2, 3, 4, 5, 6, 7, 8, 9, or 10 minutes. In embodiment, the mixing of the biological fluid and the capture solution occurs in less than 1 minute.

In some embodiments, a depletion module is used in the methods described herein in order to separate biological fluid components that are not bound by the capture agent. The depletion module optionally comprises an arrangement of posts to deplete biological fluid components that are not bound by the affinity agent. Posts may be circular or notched. In some embodiments, post structures for blood cell depletion are notched structures. In other embodiments, a depletion module is omitted from the microfluidic device. For example, where whole blood samples require depletion, other biological fluid samples such as plasma and serum may not require a separation step.

In various embodiments, the depletion of biological fluid components that are not bound by the affinity agent occurs in less than 0.5, 1, 2, 3, 4, 5, 6, 7, 8, 9, or 10 minutes. In embodiments, depletion occurs in less than 30 seconds.

Detection modules are also provided as described herein. The detection module is operably associated with an image-capturing device capable of detecting the presence of a complex (e.g., an affinity agent and a molecule of interest). Exemplary image-capturing devices include, but are not limited to, a camera (e.g., a charge-coupled device (CCD) camera or a scientific complementary metal—oxide—semiconductor sensor (CMOS or sCMOS) camera. In some embodiments, micro-beads in the detection module are focused using sheath flow and monitored in the detection region where a high-speed CCD camera is used to detect the microbeads. Fluorescence intensity is proportional to the amount of biomarkers bound to the beads, thus enabling quantitative measurements.

There are numerous ways in which the complex formation can be assessed and used to determine the presence or concentration of one or more target molecules. For example, concentration of the one or more molecules is determined in the embodiment by measuring fluorescence intensity.

In some embodiments, the height of the microfluidic channel configured to receive the biological fluid sample stream and buffer stream may be from about 1 μm to about 1000 μm, e.g., from about 25 μm to about 900 μm, from about 50 μm to about 800 μm, from about 50 μm to about 700 μm, from about 50 μm to about 600 μm, from about 50 μm to about 500 μm, from about 50 μm to about 400 μm, from about 50 μm to about 300 μm, from about 50 μm to about 200 μm, or from about 50 μm to about 100 μm.

In some embodiments, during operation of the microfluidic device, the biological fluid sample stream has a first flow rate, the buffer stream has a second flow rate, and the ratio of the second flow rate to the sum of the first and second flow rates is from about 0.1:1 to about 1:1, e.g., from about 0.2:1 to about 1:1, from about 0.3:1 to about 1:1, from about 0.4:1 to about 1:1, from about 0.5:1 to about 1:1, from about 0.6:1 to about 1:1, from about 0.7:1 to about 1:1, from about 0.8:1 to about 1:1, or from about 0.9:1 to about 1:1. In some embodiments, the ratio of the second flow rate to the sum of the first and second flow rates is from about 0.1:1 to about 0.2:1, from about 0.2:1 to about 0.3:1, from about 0.3:1 to about 0.4:1, from about 0.4:1 to about 0.5:1, from about 0.5:1 to about 0.6:1, from about 0.6:1 to about 0.7:1, from about 0.7:1 to about 0.8:1, or from about 0.8:1 to about 0.9:1. In some embodiments, the ratio of the second flow rate to the sum of the first and second flow rates is from about 1:1 to about 1:10. In some embodiments the ratio is 1:5.

Microfluidics devices according to the present disclosure may be characterized in various ways. In certain embodiments, for example, microfluidics devices have at least one "micro" channel. Such channels may have at least one cross-sectional dimension on the order of a millimeter or smaller (e.g., less than or equal to about 1 millimeter). For certain applications, this dimension may be adjusted; in some embodiments the at least one cross-sectional dimension is about 500 micrometers or less. In some embodiments, again as applications permit, the cross-sectional dimension is about 100 or 50 micrometers or less . A cross-sectional dimension is one that is generally perpendicular to the direction of centerline flow, although it should be understood that when encountering flow through elbows or other features that tend to change flow direction, the cross-sectional dimension in play need not be strictly perpendicular to flow. It should also be understood that in some embodiments, a micro-channel may have two or more cross-sectional dimensions such as the height and width of a rectangular cross-section or the major and minor axes of an elliptical cross-section. Either of these dimensions may be compared against sizes presented here.

In some embodiments, microfluidic devices according to the present disclosure are fabricated using microfabrication technology. Such technology is commonly employed to fabricate integrated circuits (ICs), microelectromechanical devices (MEMS), display devices, and the like. Among the types of microfabrication processes that can be employed to produce small dimension patterns in microfluidic device fabrication are photolithography (including X-ray lithography, e-beam lithography, etc.), self-aligned deposition and etching technologies, anisotropic deposition and etching processes, self-assembling mask formation (e.g., forming layers of hydrophobic-hydrophilic copolymers), etc.

In view of the above, it should be understood that some of the principles and design features described herein can be scaled to larger devices and systems including devices and systems employing channels reaching the millimeter or even centimeter scale channel cross-sections. Thus, when describing some devices and systems as "microfluidic," it is intended that the description apply equally, in certain embodiments, to some larger scale devices.

When referring to a microfluidic "device" it is generally intended to represent a single entity in which one or more channels, reservoirs, stations, etc. share a continuous substrate, which may or may not be monolithic. A microfluidics "system" may include one or more microfluidic devices and associated fluidic connections, electrical connections, control/logic features, etc. Aspects of microfluidic devices include the presence of one or more fluid flow paths, e.g., channels, having dimensions as discussed herein.

In various embodiments, a microfluidic device according to the present disclosure is provided comprising (i) a mixing module and (ii) a detection module. In some embodiments, a microfluidic device according to the present disclosure is provided comprising (i) a mixing module and (ii) a depletion module, and (iii) a detection module. In some embodiments, a device capable of detecting and quantifying an optical measurement is operably connected to the microfluidic device.

Various features and examples of microfluidic device components suitable for use with in connection with the disclosed microfluidic devices will now be described.

Substrate

Substrates used in microfluidic systems are the supports in which the necessary elements for fluid transport are provided. The basic structure may be monolithic, laminated, or otherwise sectioned. Commonly, substrates include one or more microchannels serving as conduits for samples and reagents (if necessary). They may also include input ports, output ports, and/or features to assist in flow control.

In certain embodiments, the substrate choice may be dependent on the application and design of the device. Substrate materials are generally chosen for their compatibility with a variety of operating conditions. Limitations in microfabrication processes for a given material are also relevant considerations in choosing a suitable substrate. Useful substrate materials include, e.g., glass, polymers, silicon, metal, and ceramics.

Polymers are standard materials for microfluidic devices because they are amenable to both cost effective and high volume production. Polymers can be classified into three categories according to their molding behavior: thermoplastic polymers, elastomeric polymers and duroplastic polymers. Thermoplastic polymers can be molded into shapes above the glass transition temperature, and will retain these shapes after cooling below the glass transition temperature. Elastomeric polymers can be stretched upon application of an external force, but will go back to original state once the external force is removed. Elastomers do not melt before reaching their decomposition temperatures. Duroplastic polymers have to be cast into their final shape because they soften a little before the temperature reaches their decomposition temperature.

Among the polymers that may be used in microfabricated devices according to the present disclosure are polydimethylsiloxane (PDMS), polyamide (PA), polybutylenterephthalate (PBT), polycarbonate (PC), polyethylene (PE), polymethylmethacrylate (PMMA), polyoxymethylene (POM), polypropylene (PP), polyphenylenether (PPE), polystyrene (PS) and polysulphone (PSU). The chemical and physical properties of polymers can limit their uses in microfluidics devices. Specifically in comparison to glass, the lower resistance against chemicals, the aging, the mechanical stability, and the UV stability can limit the use of polymers for certain applications.

Glass, which may also be used as the substrate material, has specific advantages under certain operating conditions. Since glass is chemically inert to most liquids and gases, it is particularly appropriate for applications employing certain solvents that have a tendency to dissolve plastics. Additionally, its transparent properties make glass particularly useful for optical or UV detection.

Methods of Fabrication

Microfabrication processes differ depending on the type of materials used in the substrate and the desired production volume. For small volume production or prototypes, fabrication techniques include LIGA, powder blasting, laser ablation, mechanical machining, electrical discharge machining, photoforming, etc. Technologies for mass production of microfluidic devices may use either lithographic or master-based replication processes. Lithographic processes for fabricating substrates from silicon/glass include both wet and dry etching techniques commonly used in fabrication of semiconductor devices. Injection molding and hot embossing typically are used for mass production of plastic substrates.

Glass, Silicon and Other "Hard" Materials (Lithography, Etching, Deposition)

The combination of lithography, etching and deposition techniques may be used to make microcanals and microcavities out of glass, silicon and other "hard" materials. Technologies based on the above techniques are commonly applied in for fabrication of devices in the scale of 0.1-500 micrometers.

Microfabrication techniques based on current semiconductor fabrication processes are generally carried out in a clean room. The quality of the clean room is classified by the number of particles<4 µm in size in a cubic inch. Typical clean room classes for MEMS microfabrication are 1000 to 10000.

In certain embodiments, photolithography may be used in microfabrication. In photolithography, a photoresist that has been deposited on a substrate is exposed to a light source through an optical mask. Conventional photoresist methods allow structural heights of up to 10-40 µm. If higher structures are needed, thicker photoresists such as SU-8, or polyimide, which results in heights of up to 1 mm, can be used.

After transferring the pattern on the mask to the photoresist-covered substrate, the substrate is then etched using either a wet or dry process. In wet etching, the substrate—area not protected by the mask—is subjected to chemical attack in the liquid phase. The liquid reagent used in the etching process depends on whether the etching is isotropic or anisotropic. Isotropic etching generally uses an acid to form three-dimensional structures such as spherical cavities in glass or silicon. Anisotropic etching forms flat surfaces such as wells and canals using a highly basic solvent. Wet anisotropic etching on silicon creates an oblique channel profile.

Dry etching involves attacking the substrate by ions in either a gaseous or plasma phase. Dry etching techniques can be used to create rectangular channel cross-sections and arbitrary channel pathways. Various types of dry etching that may be employed including physical, chemical, physico-chemical (e.g., RIE), and physico-chemical with inhibitor. Physical etching uses ions accelerated through an electric field to bombard the substrate's surface to "etch" the structures. Chemical etching may employ an electric field to migrate chemical species to the substrate's surface. The chemical species then reacts with the substrate's surface to produce voids and a volatile species.

In certain embodiments, deposition is used in microfabrication. Deposition techniques can be used to create layers of metals, insulators, semiconductors, polymers, proteins and other organic substances. Most deposition techniques fall into one of two main categories: physical vapor deposition (PVD) and chemical vapor deposition (CVD). In one approach to PVD, a substrate target is contacted with a holding gas (which may be produced by evaporation for example). Certain species in the gas adsorb to the target's surface, forming a layer constituting the deposit. In another approach commonly used in the microelectronics fabrication industry, a target containing the material to be deposited is sputtered with using an argon ion beam or other appropriately energetic source. The sputtered material then deposits on the surface of the microfluidic device. In CVD, species in contact with the target react with the surface, forming components that are chemically bonded to the object. Other deposition techniques include: spin coating, plasma spraying, plasma polymerization, dip coating, casting and Langmuir-Blodgett film deposition. In plasma spraying, a fine powder containing particles of up to 100 µm in diameter is suspended in a carrier gas. The mixture containing the particles is accelerated through a plasma jet and heated. Molten particles splatter onto a substrate and freeze to form a dense coating. Plasma polymerization produces polymer films (e.g. PMMA) from plasma containing organic vapors.

Once the microchannels, microcavities and other features have been etched into the glass or silicon substrate, the etched features may be sealed to ensure that the microfluidic device is "watertight." When sealing, adhesion can be applied on all surfaces brought into contact with one another. The sealing process may involve fusion techniques such as those developed for bonding between glass-silicon, glass-glass, or silicon-silicon.

Anodic bonding can be used for bonding glass to silicon. A voltage is applied between the glass and silicon and the temperature of the system is elevated to induce the sealing of the surfaces. The electric field and elevated temperature induces the migration of sodium ions in the glass to the glass-silicon interface. The sodium ions in the glass-silicon interface are highly reactive with the silicon surface forming a solid chemical bond between the surfaces. The type of glass used should ideally have a thermal expansion coefficient near that of silicon (e.g. Pyrex Corning 7740).

Fusion bonding can be used for glass-glass or silicon-silicon sealing. The substrates are first forced and aligned together by applying a high contact force. Once in contact, atomic attraction forces (primarily van der Waals forces) hold the substrates together so they can be placed into a furnace and annealed at high temperatures. Depending on the material, temperatures used ranges between about 600 and 1100 degrees C.

Polymers/Plastics

A number of techniques may be employed for micromachining plastic substrates in accordance with embodiments disclosed in the present disclosure. Among these are laser ablation, stereolithography, oxygen plasma etching, particle jet ablation, and microelectro-erosion. Some of these techniques can be used to shape other materials (glass, silicon, ceramics, etc.) as well.

To produce multiple copies of a microfluidic device, replication techniques are employed. Such techniques involve first fabricating a master or mold insert containing the pattern to be replicated. The master is then used to mass-produce polymer substrates through polymer replication processes.

In the replication process, the master pattern contained in a mold is replicated onto the polymer structure. In certain embodiments, a polymer and curing agent mix is poured onto a mold under high temperatures. After cooling the mix, the polymer contains the pattern of the mold, and is then removed from the mold. Alternatively, the plastic can be injected into a structure containing a mold insert. In micro-injection, plastic heated to a liquid state is injected into a mold. After separation and cooling, the plastic retains the mold's shape.

PDMS (polydimethylsiloxane), a silicon-based organic polymer, may be employed in the molding process to form microfluidic structures. Because of its elastic character, PDMS is well suited for microchannels between about 5 and 500 μm. Specific properties of PDMS make it particularly suitable for microfluidic purposes: 1) It is optically clear which allows for visualization of the flows; 2) PDMS when mixed with a proper amount of reticulating agent has elastomeric qualities that facilitates keeping microfluidic connections "watertight;" 3) Valves and pumps using membranes can be made with PDMS because of its elasticity; 4) Untreated PDMS is hydrophobic, and becomes temporarily hydrophilic after oxidation of surface by oxygen plasma or after immersion in strong base; oxidized PDMS adheres by itself to glass, silicon, or polyethylene, as long as those surfaces were themselves exposed to an oxygen plasma. 5) PDMS is permeable to gas. Filling of the channel with liquids is facilitated even when there are air bubbles in the canal because the air bubbles are forced out of the material. But it's also permeable to non-polar-organic solvents.

Microinjection can be used to form plastic substrates employed in a wide range of microfluidic designs. In this process, a liquid plastic material is first injected into a mold under vacuum and pressure, at a temperature greater than the glass transition temperature of the plastic. The plastic is then cooled below the glass transition temperature. After removing the mold, the resulting plastic structure is the negative of the mold's pattern.

Yet another replicating technique is hot embossing, in which a polymer substrate and a master are heated above the polymer's glass transition temperature, Tg (which for PMMA or PC is around 100-180 degrees C.). The embossing master is then pressed against the substrate with a preset compression force. The system is then cooled below Tg and the mold and substrate are then separated.

Typically, the polymer is subjected to the highest physical forces upon separation from the mold tool, particularly when the microstructure contains high aspect ratios and vertical walls. To avoid damage to the polymer microstructure, material properties of the substrate and the mold tool may be taken into consideration. These properties include: sidewall roughness, sidewall angles, chemical interface between embossing master and substrate and temperature coefficients. High sidewall roughness of the embossing tool can damage the polymer microstructure since roughness contributes to frictional forces between the tool and the structure during the separation process. The microstructure may be destroyed if frictional forces are larger than the local tensile strength of the polymer. Friction between the tool and the substrate may be important in microstructures with vertical walls. The chemical interface between the master and substrate could also be of concern. Because the embossing process subjects the system to elevated temperatures, chemical bonds could form in the master-substrate interface. These interfacial bonds could interfere with the separation process. Differences in the thermal expansion coefficients of the tool and the substrate could create addition frictional forces.

Various techniques can be employed to form molds, embossing masters, and other masters containing patterns used to replicate plastic structures through the replication processes mentioned above. Examples of such techniques include LIGA (described below), ablation techniques, and various other mechanical machining techniques. Similar techniques can also be used for creating masks, prototypes and microfluidic structures in small volumes. Materials used for the mold tool include metals, metal alloys, silicon and other hard materials.

Laser ablation may be employed to form microstructures either directly on the substrate or through the use of a mask. This technique uses a precision-guided laser, typically with wavelength between infrared and ultraviolet. Laser ablation may be performed on glass and metal substrates, as well as on polymer substrates. Laser ablation can be performed either through moving the substrate surface relative to a fixed laser beam, or moving the beam relative to a fixed substrate. Various micro-wells, canals, and high aspect structures can be made with laser ablation.

Certain materials such as stainless steel make very durable mold inserts and can be micromachined to form structures down to the 10 μm range. Various other micro-machining techniques for microfabrication exist including μ-Electro Discharge Machining (μ-EDM), μ-milling, focused ion beam milling. μ-EDM allows the fabrication of 3-dimensional structures in conducting materials. In μ-EDM, material is removed by high-frequency electric discharge generated between an electrode (cathode tool) and a workpiece (anode). Both the workpiece and the tool are submerged in a dielectric fluid. This technique produces a comparatively rougher surface but offers flexibility in terms of materials and geometries.

Electroplating may be employed for making a replication mold tool/master out of, e.g., a nickel alloy. The process starts with a photolithography step where a photoresist is used to defined structures for electroplating. Areas to be electroplated are free of resist. For structures with high aspect ratios and low roughness requirements, LIGA can be used to produce electroplating forms. LIGA is a German acronym for Lithographic (Lithography), Galvanoformung (electroplating), Abformung (molding). In one approach to LIGA, thick PMMA layers are exposed to x-rays from a synchrotron source. Surfaces created by LIGA have low roughness (around 10 nm RMS) and the resulting nickel tool has good surface chemistry for most polymers.

As with glass and silicon devices, polymeric microfluidic devices may be sealed before they become functional. Lamination is one method used to seal plastic microfluidic devices. In one lamination process, a PET foil (about 30 μm) coated with a melting adhesive layer (typically 5-10 μm) is rolled with a heated roller, onto the microstructure. Through this process, the lid foil is sealed onto the channel plate. Several research groups have reported a bonding by polymerization at interfaces, whereby the structures are heated and force is applied on opposite sides to close the channel. But excessive force applied may damage the microstructures. Both reversible and irreversible bonding techniques exist for plastic-plastic and plastic-glass interfaces. One method of reversible sealing involves first thoroughly rinsing a PDMS substrate and a glass plate (or a second piece of PDMS) with methanol and bringing the surfaces into contact with one another prior to drying. The microstructure is then dried in an oven at 65.degree. C. for 10 min. No clean room is required for this process. Irreversible sealing is accomplished by first thoroughly rinsing the pieces with methanol and then drying them separately with a nitrogen stream. The two pieces are then placed in an air plasma cleaner and oxidized at high power for about 45 seconds. The substrates are then brought into contact with each other and an irreversible seal forms spontaneously.

Other available techniques include laser and ultrasonic welding. In laser welding, polymers are joined together through laser-generated heat. This method has been used in the fabrication of micropumps. Ultrasonic welding is another bonding technique that may be employed in some applications.

In various embodiments, a biomarker monitoring system is provided by the present disclosure comprising a microfluidic device, wherein said microfluidic device comprises at least two inlets that form a single lane, wherein one inlet is capable of intermittently or continuously flowing a biological fluid from a subject and wherein one inlet is capable of intermittently or continuously flowing a solution comprising a capturing agent; wherein the lane comprises: a mixing module for mixing the biological fluid and a capturing agent capable of forming a complex with one or more biomarkers present in the biological fluid; optionally a depletion module for depleting biological fluid components that are not bound by the capture agent; and a detection module for detecting the presence of a complex between a biomarker and a capturing agent; wherein at least the detection module is operably associated with an image-capturing device capable of one or more optical measurements. In other embodiments, the aforementioned biomarker monitoring system is provided wherein at least one inlet is operably connected to a subject to allow continuous flow of a biological fluid into the mixing module. In other embodiments, the biomarker monitoring system is provided further comprising a feedback loop in communication with the device and capable of intermittently or continuously flowing a therapeutic solution to the subject. In some embodiments, the therapeutic solution comprises a therapeutic biomolecule or pharmaceutical.

The following examples are offered by way of illustration, and not by way of limitation.

EXAMPLES

The biosensor described herein and in the following examples is the first real-time biosensor that can continuously and simultaneously measure multiple target molecules directly in whole blood. One embodiment of the present disclosure is provided in FIG. 1 which depicts various embodiments of the continuous, real-time monitoring methods and exemplary device provided by the present disclosure. In the example provided in FIG. 1, the RTCM device measures transient changes in glucose and insulin levels. The upper portion of FIG. 1 shows 15 μm microbeads functionalized with either glucose (left) or insulin (right) probes. By way of example, a glucose aptamer strand conjugated with Cy5 fluorophore and a DNA competitor conjugated with a quencher (BHQ2) are hybridized to form the aptamer-DNA competitor complex (signal off). In this way, in the presence of glucose, the DNA competitor strand with quencher is displaced, causing the bead to fluoresce. Alternatively and in another embodiment, a sandwich ELISA consisting of the capture antibodies, insulin, and fluorescently tagged detection antibodies is formed on the microbeads to quantify insulin levels. The lower portion of FIG. 1 shows a biosensor connected to a subject (e.g., a rat through an angio-catheter) and the subject's blood is injected into the device using a peristaltic pump. The real-time monitoring of targets (e.g., molecules or biomolecules as described herein) is achieved through the combination of three main modules: (1) a mixing module where the blood sample containing the targets is mixed with reagents, (2) a depletion module which depletes blood cells, and (3) a focusing module which transfers the fluorescently labeled beads to the detection window.

The following materials and methods were used in Experiments 1-4, herein.

RTCM Device Fabrication

The RTCM device integrates three modules to achieve continuous, real-time monitoring: (1) a mixing module, which combines molecular probes for analyte detection with the whole blood sample; (2) a depletion module, which minimizes background by reducing the number of blood cells in the sample; and (3) a focusing module, which brings the target to the detection window and quantitatively measures its abundance (FIG. 1).

Figures 2A, 2B, 2C:
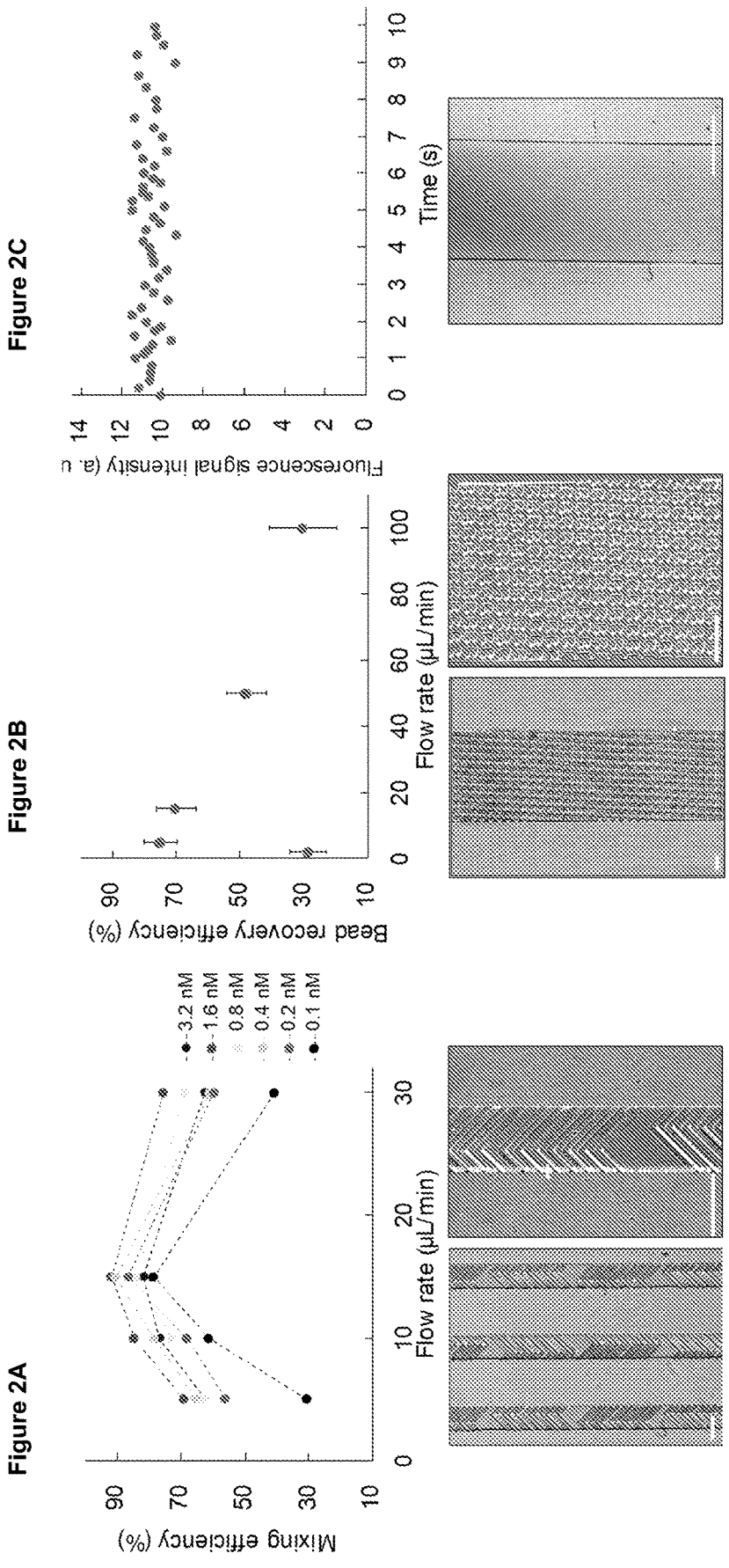
FIGS. 2A-2E show the testing and optimizing the core components of RTCM.
Figure 2D:
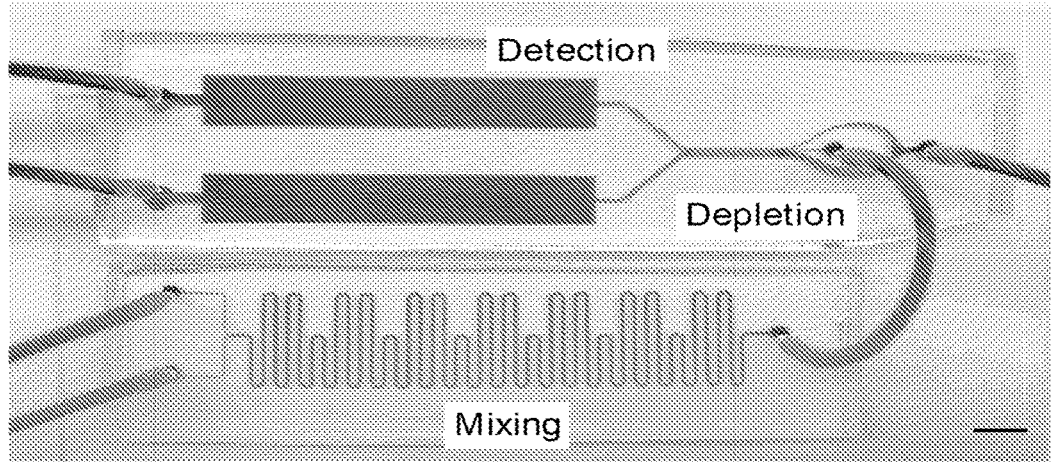
Figure 2E:
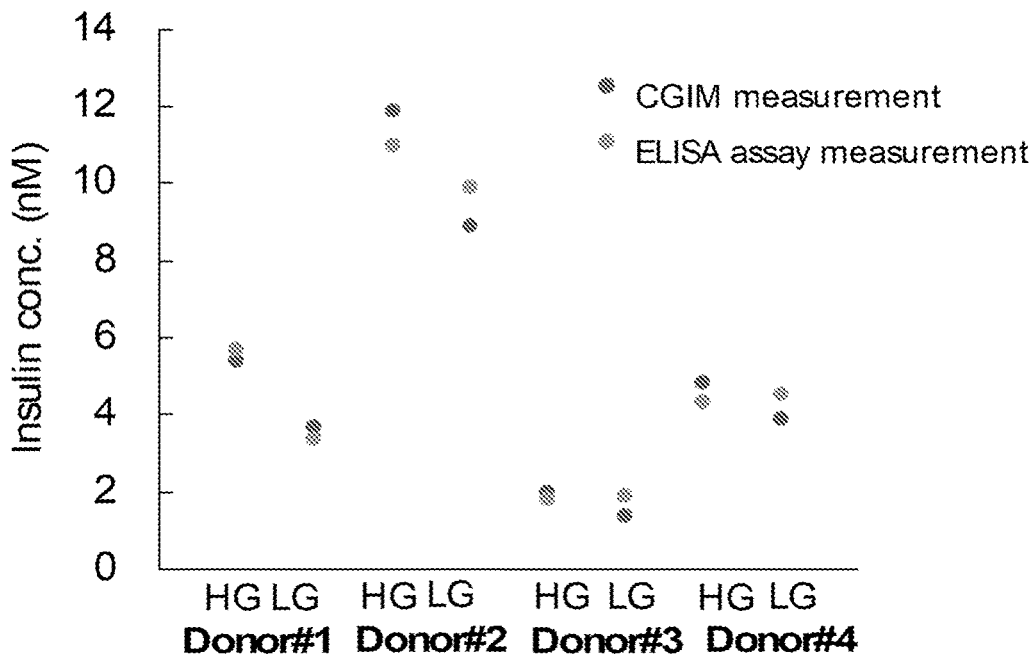

Glass substrates and polydimethylsiloxane (PDMS) were used with a standard microfluidic device fabrication protocol to build RTCM device. Prior to fabricating the full RTCM device, the individual device compartments were first optimized: the mixing, depletion, and detection modules. The mixing module achieves rapid and continuous mixing of reagents through the use of serpentine channels with optimized length, and which incorporate herringbone structures inside the channel (FIG. 2A, bottom). This dramatically enhances the rate of molecular diffusion and reduces the required incubation time to less than one minute. Different concentrations of insulin were injected into the mixing module through the sample inlet, and injected a solution of fluorescently-tagged detection antibodies and microbeads functionalized with the insulin capture antibody through the reagent inlet. These solutions were injected at a variety of different flow-rates, and then collected the beads from the module outlet and observed them under a fluorescence microscope. After comparing the fluorescence signal intensity obtained at different flow-rates with the intensity achieved with standard bench-top incubation (FIG. 3A, top), optimal mixing was observed at a flow rate of 15 μL/min, with a total mixing time of 30 sec. At lower or higher flow-rates, mixing is not as effective as bench-top incubation.

The depletion module is designed to not only eliminate blood cells, but also free fluorescently-tagged antibodies, thereby reducing the background. This module (FIG. 2B) employs deterministic lateral displacement (DLD) sorting to isolate beads from blood cells. DLD is an established hydrodynamic approach for separating particles based purely on size in a continuous manner. DLD utilizes specific arrangements of posts within a channel to facilitate separation of particles larger and smaller than a critical diameter $(D_c)$ by precisely controlling their trajectory within the device. In this scenario, the $D_c$ is 15 μm based on the diameter of the microbeads used for target capture, and a device design was sought that would allow isolation of these beads amid a far larger number of blood cells, which are smaller than 15 μm. Notched and post structures were tested, and a sheath buffer solution was introduced along with the sample into the device for bead recovery and blood cell depletion. The best performance was observed at a sample flow-rate of 5-20 μL/min and sheath buffer:sample flow-rate ratio of 5:1 (FIG. 2B, top). At higher or lower inlet flow-rates, the depletion performance worsened.

In the detection module, the target-bound beads flow into a detection window (FIG. 2C, bottom), and their fluorescence intensity is continuously measured with a high-speed camera under spatially-multiplexed two-color laser illumination (see Methods and Supplementary Information). Incoming beads are illuminated by a red laser first, which interrogates the Cy5 fluorescence intensity that indicates glucose concentration. This is followed by illumination with a green laser that interrogates the R-PE fluorescence intensity, which indicates insulin concentrations. An exposure time of 50 ms was used and acquired images every 100 ms. Fluorescently-labeled microbeads were introduced into the detection module and the fluorescence signal intensity and the number of beads passing through the detection window over a short time scale were measured. On average, 5 beads per second passed through the detection window, indicating the temporal resolution of 200 ms for the RTCM or CGIM device (FIG. 2C, top). The fast frame-rate and high sensitivity of the camera allow us to continuously track individual microbeads, enabling quantitative detection of analytes in real-time. Finally, the three modules were combined to produce the integrated RTCM device (FIG. 3D). To achieve this, the fluidic resistance between the different modules was simulated and adjusted.

Integrated RTCM or CGIM Device Fabrication

In order to fabricate the integrated RTCM or CGIM platform, we first connected the mixer and depletion modules and tested their performance in capturing insulin from whole blood samples and the isolation of target-bound beads. Blood spiked with 3 nM insulin was injected through the sample inlet at 15 μL/min, while the reagent solution containing functionalized microbeads and detection antibodies was injected through the reagent inlet at the same flow-rate. The mixer outlet was connected to the depletion sample inlet, and as the mixture entered the depletion module, a buffered solution was injected at 75 μL/min to form the required sheath flow for separation. The flow-rates were optimized to achieve the best mixing efficiency, bead recovery, and blood cell depletion. The beads were collected from the depletion outlet and monitored via fluorescence microscopy.

The connection of the depletion and detection modules was tested prior to full integration. A dummy detection module was connected to the blood waste outlet to adjust outlet resistance, ensuring vertical fluid flow through the depletion device. The detection window was designed to have a width of 292 μm in order to accommodate the 20× objective field used for fluorescence measurement. The detection module was then widened to 4.8 mm, to prevent clogging by the high number of blood cells/beads passing through the channel. The optimized dimensions of the modules in the final device are summarized in Table 1.

TABLE 1

| Dimensions of fabricated modules of CGIM device | |
| --- | --- |
| Mixer module | |
| Sample & reagent inlet width | 150 μm |
| Channel width | 300 μm |
| Outlet width | 150 μm |
| Serpentine channel length | 30 cm |
| Depletion module | |
| Sample inlet width | 150 μm |
| Total channel width | 850 μm |
| Channel length | 7.5 mm |
| Pillar to pillar distance (λ) | 55 μm |
| Gap (horizontal) | 30 μm |
| Gap (vertical) | 22 μm |
| Periodicity [# rows] | 10 |
| Offset between pillar rows | 11 degrees |
| Theoretical critical diameter | 14 μm |
| Detection module | |
| Small (main) channel width | 292 μm |
| Large channel width | 4800 μm |

Materials

All chemicals were purchased from Sigma-Aldrich Co. (St. Louis, MO), unless otherwise noted. Streptavidin coated microbeads (15 μm, CP01008, Bangslab), human whole blood sample (BioIVT), matched paired insulin antibodies (capture Ab: BM364-Z8A2, detection Ab: BM364-T8F5, BBI solutions), human insulin (3435/10, R&D Systems), Streptozotocin (MedChem Express), Recombinant human insulin (Humulin R, Eli Lilly), neutral protamine hagedorn recombinant human insulin (NPH insulin) (Humulin H, Eli Lilly), R-PE antibody conjugation kit (P-9002-002, TriLink Biotechnologies), Oligonucleotides (Integrated DNA Technologies, IA) for glucose measurements are summarized in Table 2.

| | |
| --- | --- |
| Glucose aptamer (SEQ ID NO: 1) | /5Biosg//iCy5/CTC TCG GGA CGA CCG TGT GTG TTG CTC TGT AAC AGT GTC CAT TGT CGT CCC |
| Quencher strand (SEQ ID NO: 2) | GGT CGT CCC GAG AG/3BHQ2/ |

Microbead Functionalization

15-μm SuperAvidin™-coated microspheres (Bangs Laboratories) were functionalized with monoclonal biotinylated anti-insulin capture antibodies (cAbs) (BBI Solutions) as directed by the bead manufacturer's recommended coating protocol. Briefly, a typical coating procedure for 10 mg of microspheres commenced with homogenizing the bead stock solution on a rotator, transferring 1 mL of the 10 mg/mL stock to a new tube, adding 10 mL of 1× PBS+0.05% Tween 20 (PBST, pH 7.4), mixing by pipetting or vortexing, centrifuging at 2100 rcf for 5 min, and removing the supernatant. The second wash was performed in the same manner. Beads were then resuspended in 20 mL PBS+0.05% BSA+0.01% Tween 20 (PBSBT), and incubated with 1.2 nM biotinylated cAb, calculated such that the cAb was in significant excess (1.5-2 μg cAb/mg beads) compared to the amount required to form a monolayer on the surface of each bead in the reaction. The mixture was briefly vortexed or pipetted to homogeneity and incubated at room temperature on a rotator for 30 min. Following this, the beads were pelleted via centrifugation at 2100 rcf for 5 min and washed thrice with 10 mL PBST as described above. After the final wash buffer supernatant was removed, the beads were resuspended in PBSBT at a concentration of 10 mg/mL and stored at 4° C. until used. For glucose capture, first the glucose aptamer strand conjugated to the Cy5 dye was hybridized to the DNA competitor strand which is conjugated to the quencher at a ratio of 1:10. Then, the microbeads were functionalized with the aptamer-DNA competitor complex through the same steps for insulin bead preparation.

Insulin Fluorescence-Based Sandwich Immunoassay

A matched sandwich pair of monoclonal anti-human insulin antibodies (Abs) was purchased from BBI Solutions (Crumlin, UK). The detection Ab (dAb) was site-specifically labeled with R-Phycoerythrin (R-PE) using a SiteClick™ R-PE Antibody Labeling Kit (Invitrogen™) according to the kit manufacturer's instructions. This method achieves site-specific labeling of immunoglobulin (IgG) Abs by targeting the carbohydrate domains found on the heavy chain of the Fc region of nearly all IgG Abs. To accomplish this, β-Galactosidase is used to remove terminal galactose residues on the N¬-linked sugars in this region. Next, an azide-containing sugar (GalNAz) is attached to the terminal GlcNAc residues now present in the carbohydrate domain via a reaction catalyzed by β-1,4-galactosyltransferase (Gal-T). The resultant azide-modified Ab is then reacted with dibenzocyclooctyne (DIBO)-modified R-PE, which reacts with the terminal azide moieties via a copper-free click reaction to produce an Ab with R-PE molecules covalently conjugated to the Fc region of the Ab, leaving the antigen-binding sites of the Ab intact. R-PE-dAb conjugates were used without further purification or extensive characterization as both the commercial and literature (Zeglis B M, Davis C B, Aggeler R, et al. Enzyme-mediated methodology for the site-specific radiolabeling of antibodies based on catalyst-free click chemistry; Bioconjug Chem. 2013; 24(6):1057-1067. doi: 10.1021/bc400122c) sources indicate this reaction scheme is highly reproducible, robust, and perhaps even quantitative, producing conjugates with an average of just under 3 R-PE molecules per Ab. Having conjugated the detection Ab with the R-PE fluorophore and functionalized microbeads with the capture Ab, these complexes were used in either benchtop incubation or RTCM device to form insulin fluorescence-based sandwich immunoassay.

Imaging Setup

A compact fluorescent microscope with spatially multiplexed two-color laser illumination and wide-field high-speed fluorescent imaging was used to measure the fluorescence of the beads. A Nikon CFI Plan Apo VC 20X Air 0.75 NA UV objective focuses two diode lasers, 520 nm/40 mW and 642 nm/5 mW with proper excitation filters, to a size of ~500 by 100 μm at the sample plane. The two laser spots have a spatial offset of ~500 μm along the bead flow direction to enable spatially multiplexed two-color fluorescent readout. The entire field of view covering both spots are imaged continuously by a high-speed, high-sensitivity scientific CMOS camera (Photometrics Prime 95B, USA) after proper two-pass-band emission filters. Incoming beads are illuminated by the 642 nm laser first, which interrogates the Cy5 fluorescence intensity that indicates real-time glucose concentrations, before being illuminated by the 520 nm laser which interrogates the PE fluorescence intensity that indicates insulin concentrations.

In Vitro Glucose Stimulated Insulin Secretion Assays

Batches of 150 primary human islets were used for in vitro secretion assays at 37 degree. All secretion assay used RPMI 1640 (Thermo Fisher Scientific) based media, supplemented with 0.5% (v/v) fetal bovine serum (HyClone), 0.2% (w/v) bovine serum albumin (Sigmar-Aldrich) and D-glucose at indicated concentrations. Human islets were incubated at a glucose concentration of 2.8 mM for 2×45 min as initial equilibration period. Subsequently, human islets were incubated at 2.8 mM (low) and 16.7 mM (high) glucose concentrations for 60 min each. At the end of each incubation, supernatant were carefully collected for later insulin quantitation by either a conventional human insulin ELISA kit (Mercodia) or RTCM or CGIM device.

Derivation of the LOD

In order to estimate the LOD of RTCM or CGIM device for glucose and insulin measurements, st, the fluorescence signal intensity was measured from the blank sample and calculated the $FL_L$ using eq. 1. A standard was then used curve to calculate the LOD.

$$FL_L = mean_{blank} + 3 \times SD_{blank}$$

Continuous, In-Vitro Monitoring of Glucose and Insulin in Whole Blood

Human blood samples were purchased from the BioIVT and spiked with different concentrations of glucose and insulin for in-vitro tracking. Prior to the experiments, blood glucose was measured using a handheld glucose meter and considered to calculate the spiked glucose concentrations. Reagent solution consisting of microbeads functionalized with insulin capture antibodies, PE-tagged insulin detection antibodies, and microbeads functionalized with the glucose aptamer hybridized with the quencher strand was prepared. Different concentrations of glucose and insulin ([Glucose, insulin]: [15 mM, 1.6 nM]; [5 mM, 0.4 nM]; [10 mM, 0.8 nM]; [8 mM, 0.2 nM]; [20 mM, 1 nM)]) were spiked into the whole blood and injected into the device sequentially. Spiked blood samples and reagent solution were injected through the inlets of mixer device at the flow rate of 15 μL/min. As bead-analyte complex pass through the detection modules, red and green laser illuminates the channel to excite Cy5 fluorophore for glucose and PE fluorophore for insulin monitoring, respectively. A high-speed CCD camera was employed to measure the fluorescence signal intensity. Between the changing of sample, buffered solution was injected into the device for 4 mins. A blank sample (with no spiked insulin or glucose) was run through the device to measure the fluorescence signal intensity from endogenous insulin and it was subtracted from the measured signal at each concentration. At the end of experiment, the images were collected, and the custom-written program was used to measure the fluorescence signal intensity. Then, the derived standard curves were employed to calculate the absolute concentrations.

Image Analysis

A method for processing the images taken from the RTCM device was developed. The images record the fluorescence intensity of bead-target complex. This reflects the target abundance inside the whole blood sample. The intensity of the light recorded from the beads passing through the detection window was estimated via the following steps.

1—Estimating the background intensity: The laser used for illuminating the sample has a profile that needed to be estimated first so that we can subtract it from the measured intensity in order to obtain the microbead fluorescence intensity. An image that is the median intensity of each pixel across all the recorded frames at different times was constructed. A smoothing Gaussian filter was then applied with a small 5×5 kernel to this image to estimate the background intensity.

2—Localizing the beads: Once background intensity is estimated, the background intensity was subtracted from each frame and then sought for connected components of high intensity within each frame to localize the beads. A threshold on the intensity level was the used to obtain a binary mask and applied another threshold on the size of the connected component to localize the beads in each frame. These two hyperparameters, i.e., the threshold on the intensity and the threshold on the size of the bead, would need to be tuned for different applications.

3—Statistics of the beads: The intensity profile was calculated over all beads, and computed several statistics, such as mean, median, and standard deviation. Data was exported into a CSV file for further processing (e.g., using Excel).

4—Producing a video localizing the beads: The edges of each bead, i.e., connected component from step 2, were determined to find the edges of each bead. The frame was processed to highlight the edge of the bead. We also save all of these processed frames in a new video (avi format). This provides a visual way of viewing the detected beads and also could be used as a way to tune the two hyperparameters involved in step 2 for localizing the beads.

These steps are implemented in Python. The code and notebook for these steps and performing the images analysis can be found on GitHub.

Streptozotocin Induced Model of Diabetes in Rats

Male Sprague Dawley rats (Charles River) were used for experiments. Animal studies were performed in accordance with the guidelines for the care and use of laboratory animals; all protocols were approved by the Stanford Institutional Animal Care and Use Committee. The protocol used for STZ induction adapted from the protocol by Kenneth K. Wu and Youming Huan (Wu, K. K., & Huan, Y. Streptozotocin-induced diabetic models in mice and rats. *Curr. Protoc. Pharmacol.* 5, 1-14 (2008)). Briefly, male Sprague Dawley rats 160-230 g (8-10 weeks) were weighed and fasted 6-8 hours prior to treatment with STZ. STZ was diluted to 10 mg/mL in the sodium citrate buffer immediately before injection. STZ solution was injected intraperitoneally at 65 mg/kg into each rat. Rats were provided with water containing 10% sucrose for 24 hours after injection with STZ. Rat blood glucose levels were tested for hyperglycemia daily after the STZ treatment via tail vein blood collection using a handheld Bayer Contour Next glucose monitor (Bayer). Diabetes was defined as having 3 consecutive blood glucose measurements >400 mg/dL in non-fasted rats.

Continuous Monitoring of Glucose and Insulin in Diabetic Rats

Diabetic rats were fasted for 4-6 hours. Rats were anesthetized using iso-fluorine (1-3%) and a catheter (20 G) was inserted into the femoral vein. Immediately after catheterization, the catheter was connected to a peristaltic pump at a flow rate of 15 µL/min. Once the tubing was primed with blood, the device was connected, and the rats were injected subcutaneously with the following formulations: (i) Humulin R (recombinant human insulin) (1 U/kg) or (ii) Humulin N (neutral protamine Hagedorn human insulin) (2 U/kg). As the blood entered the device, reagent solution was injected through a reagent inlet and were efficiently mixed inside the mixer module to capture and fluorescently labeled insulin and glucose. Subsequently, the bead-analytes complex was separated from the blood cells using the depletion module and next, the microbeads were flown into the detection module and their fluorescence intensity was continuously measured using a high speed, CCD camera for different times depending the experimental condition. At the end, images were collected, and a custom-developed program was employed to quantitatively measure the fluorescence signal intensity. Then the glucose and insulin absolute concentrations were calculated using the standard curve relating the fluorescence signal intensity to the concentration. Before injection, baseline blood glucose was measured using a handheld glucose meter and blood was sampled for ELISA. After injection, blood was sampled every 5 mins for up to 120 mins. Blood glucose was measured using a handheld blood glucose meter (Bayer) and additional blood was collected in serum tubes (Starstedt) for analysis with ELISA (Insulin ELISA, Mercodia).

Example 1

Glucose and Insulin Probes Validation

Figures 3A, 3B:
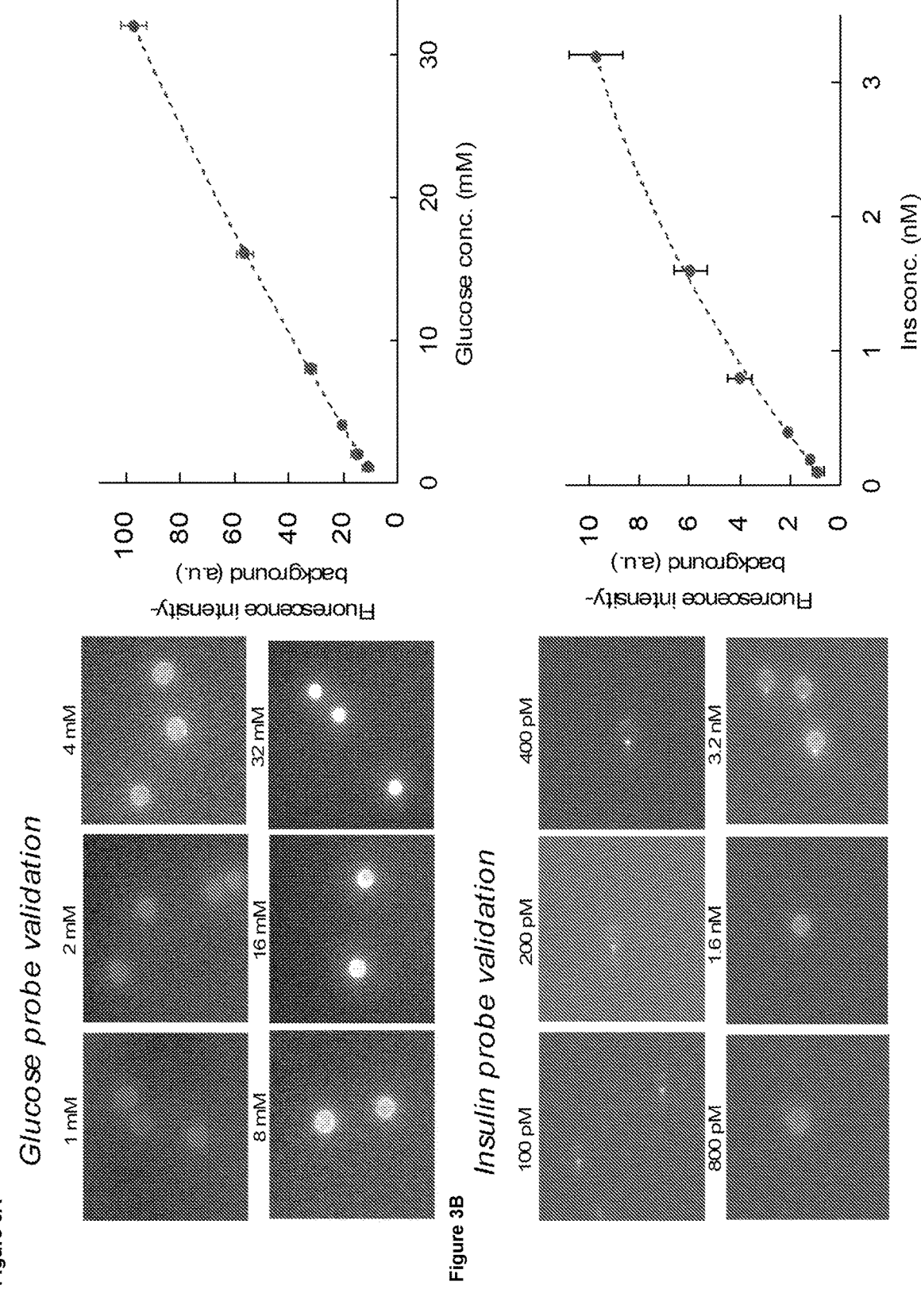
FIGS. 3A-3C show glucose probe validation: microbeads functionalized with the aptamer-DNA competitor complex were incubated with different concentrations of glucose in buffered solution. After an hour incubation, beads were washed three times and monitored under the imaging setup with red laser excitation to excite Cy5 fluorophore (left) and the fluorescence signal intensity was measured for different concentrations (right).
Figure 3C:
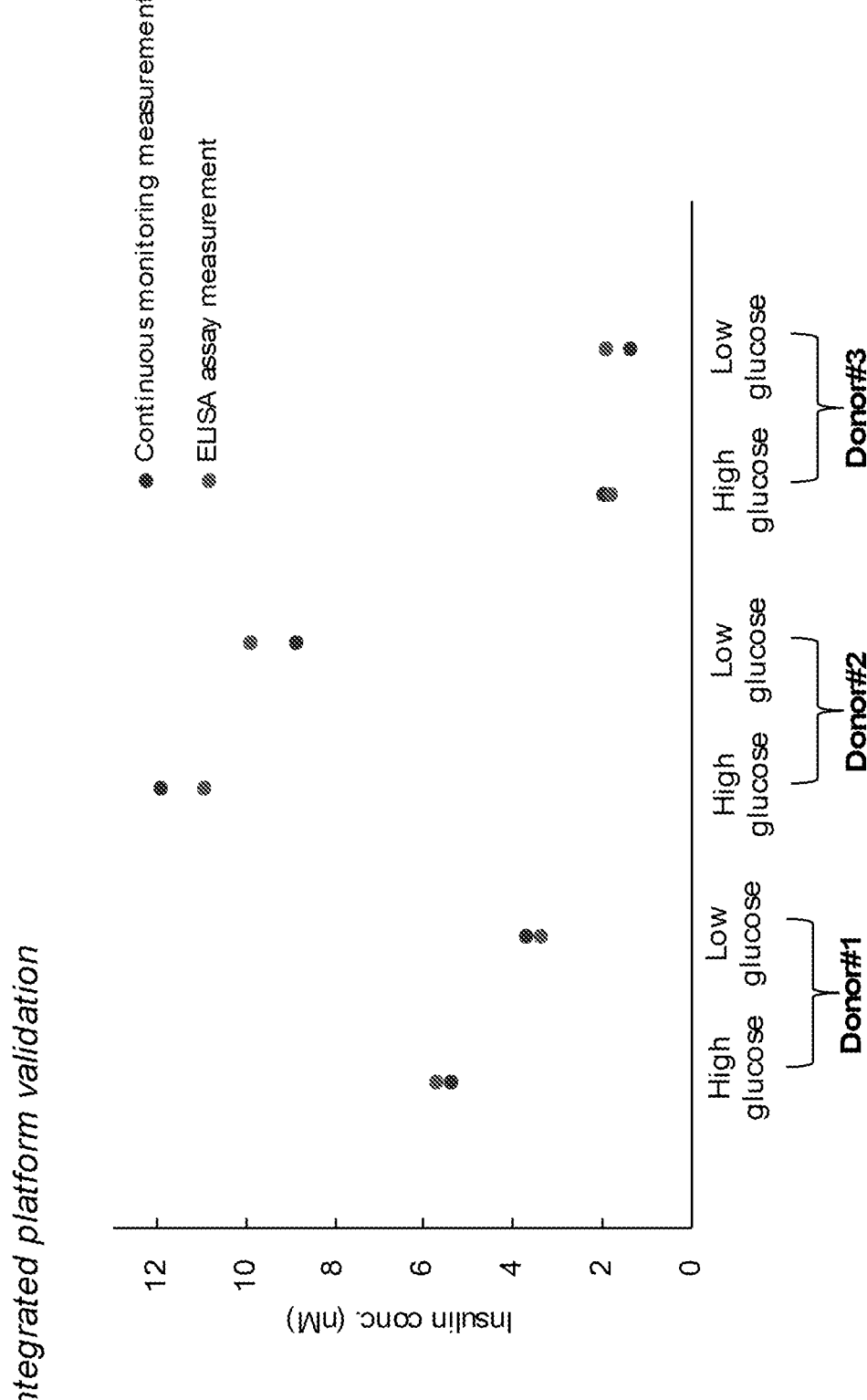

This Example demonstrates validation of the glucose and insulin probes in buffered solutions. Briefly, functionalized microbeads were prepared with the aptamer-DNA competitor complex for glucose detection or insulin capture antibodies. Then, the functionalized beads were incubated with either different concentrations of glucose (FIG. 3A) or different concentrations of insulin and the fluorescently tagged detection antibodies (FIG. 3B). After an hour of bench-top incubation, the bead-target complex was observed under the fluorescence microscope in the stationary state. The RTCM platform was fabricated, first, by optimizing the individual device modules as described herein and then combined to develop the integrated RTCM device. To achieve this, the fluidic resistance between the different modules was simulated and adjusted and optimized to generate the fully automated device. In order to characterize the performance of the system, measurements derived from the device were compared to conventional ELISA by measuring the insulin levels from an in-vitro secretion assay from human islet cells. Human islet cells were stimulated with high or low glucose containing cell media to stimulate insulin secretion. After stimulation, the supernatants were collected, and insulin concentration was measured using both the RTCM device and a conventional ELISA assay. The secretion assay experiment was performed using the islets from three different donors and as shown in FIG. 3C, the measurements obtained from the RTCM device were well-matched with the ones from the ELISA assay, demonstrating the capability of the biosensor to measure endogenous human insulin.

Example 2

Continuous, In-Vitro Glucose and Insulin Measurements in Whole Blood

This Example demonstrates the ability of the RTCM device to take continuous measurements. Known concentrations of insulin and glucose were spiked into human whole blood. A standard curve was constructed to relate fluorescence signal intensity to glucose or insulin concentration in whole blood (FIGS. 4A and 4B, insets). RTCM achieves a limit of detection of 3.7 mM and 93 pM for glucose and insulin measurements, respectively. RTCM is the first continuous monitoring biosensor that achieves the precision needed to measure a low abundance molecule like insulin directly in the blood. Different concentrations of glucose and insulin were then introduced in a whole blood sample and the RTCM device tracked concentrations for approximately 30 mins. During the experiment, the measured concentration differed from the known concentration on average by 250 μM and 24 pM for glucose and insulin measurements, respectively; verifying its ability to quantify unknown concentrations continuously and in real-time. This standard deviation is sufficiently small that the present system can be employed to reliably quantify glucose and insulin in diabetic patients, where postprandial concentrations are typically more than 3.5 mM and 300 pM, respectively.

Example 3

Continuous, In-Vivo Glucose and Insulin Measurements

Figure 5A:
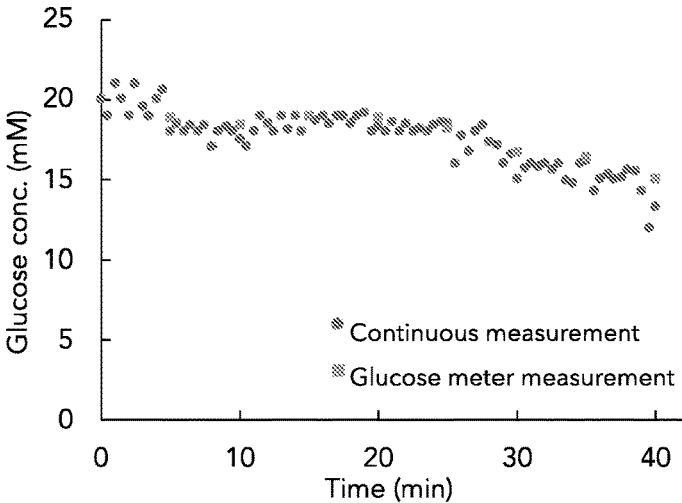
Figure 5B:
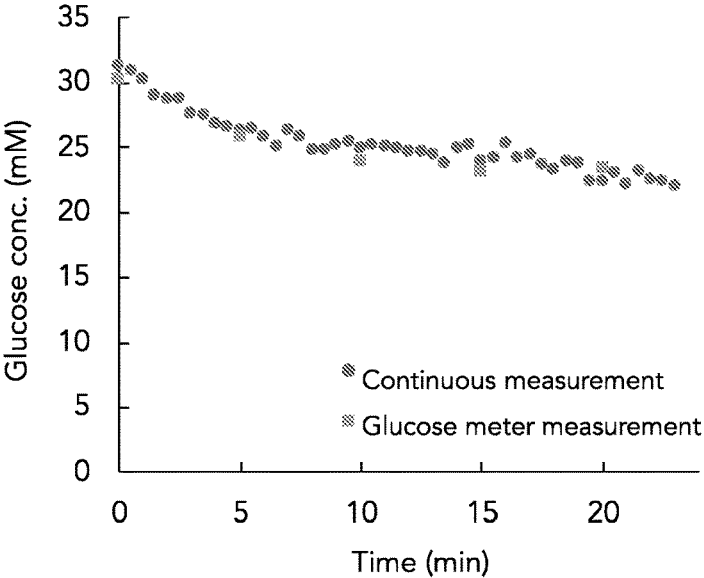
Figures 5D, 5E, 5F:
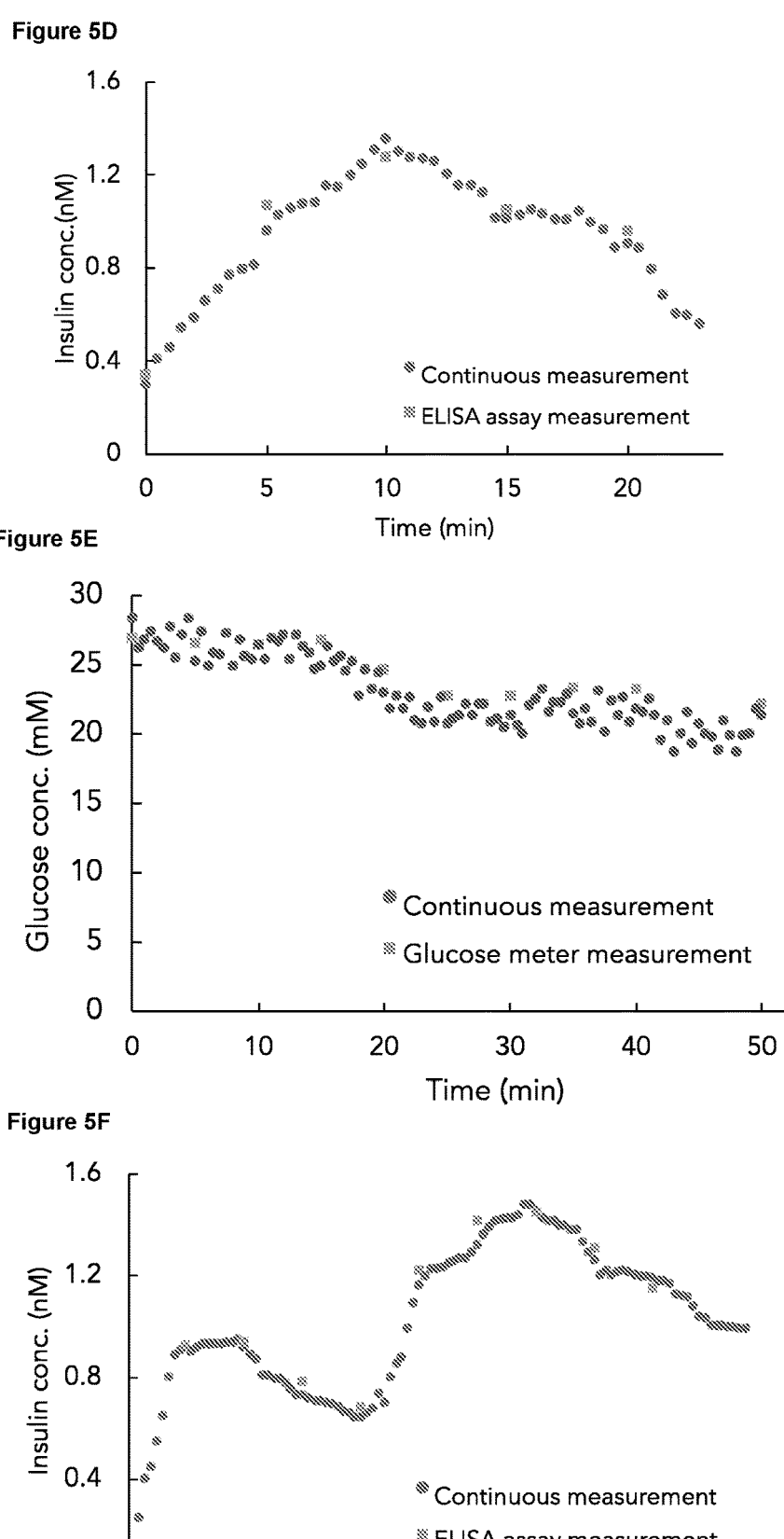

Having demonstrated the RTCM platform's ability to sensitively and accurately detect insulin and glucose in vitro, its performance in vivo in a streptozotocin-induced rat model of insulin-deficient diabetes was evaluated. This model was chosen because it lacks endogenous insulin, eliminating the potential of background due to antibody cross-reactivity. The device was connected to an anesthetized rat by a femoral venous catheter. Humulin R (recombinant human insulin) boluses were given at one (t=0) or two timepoints (t=0 and 20 min), while continuous, real-time monitoring of glucose (FIG. 5A, C, E) and insulin (FIG. 5B, D, F) levels was performed over the course of 30 to 50 mins. In experiments monitoring only a single insulin bolus (FIG. 5A, C), baseline insulin measurements were elevated due to insulin boluses given 40 minutes prior to the experiment. Peak insulin concentrations were detected at either 5 min (FIG. 5B) or 10 min (FIG. 5D) after single insulin injections. After two successive bolus injections, peak insulin concentrations were observed at 10 and 35 minutes (FIG. 5F). In parallel, we compared the RT-ELISA results with conventional ELISA analysis of insulin in blood samples collected from the rat tail vein every 5 mins and glucose measurements from a handheld glucose monitor, and observed that both sets of results correlate well.

The differences between peak insulin action in individual rats clearly show the variability in insulin pharmacokinetics, even under controlled conditions with genetically similar animals. This has important implications for human patients, who are genetically diverse, use different injection sites, and have different environmental conditions, exacerbating this inter-individual variability. Thus, these results highlight the necessity of personalized insulin monitoring.

Figure 6A:
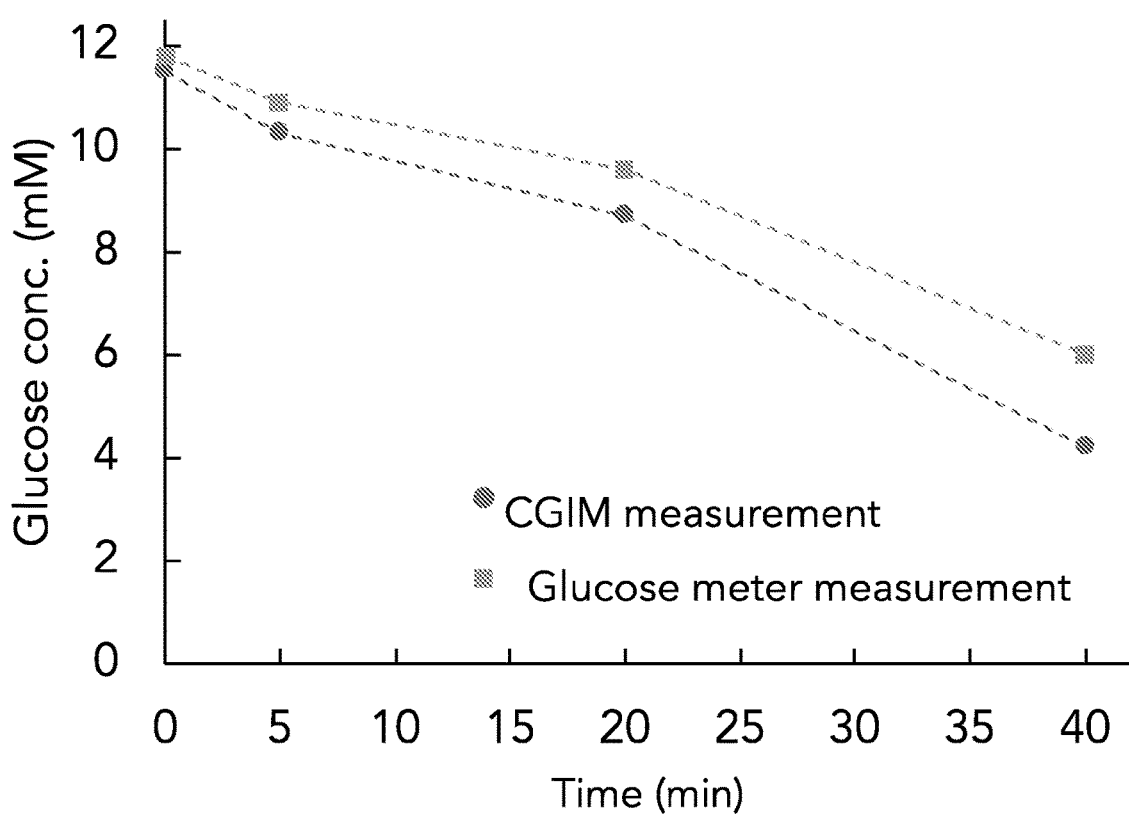
FIGS. 6A-6B show glucose and insulin measurements in an awake diabetic rat. An awake diabetic rat was injected with human insulin, with blood samples collected at t=0, 5, 20, and 40 min after injection. Glucose levels were measured using RTCM and glucose meter (FIG. 6A), and insulin levels were measured using RTCM and ELISA (FIG. 6B).
Figure 6B:
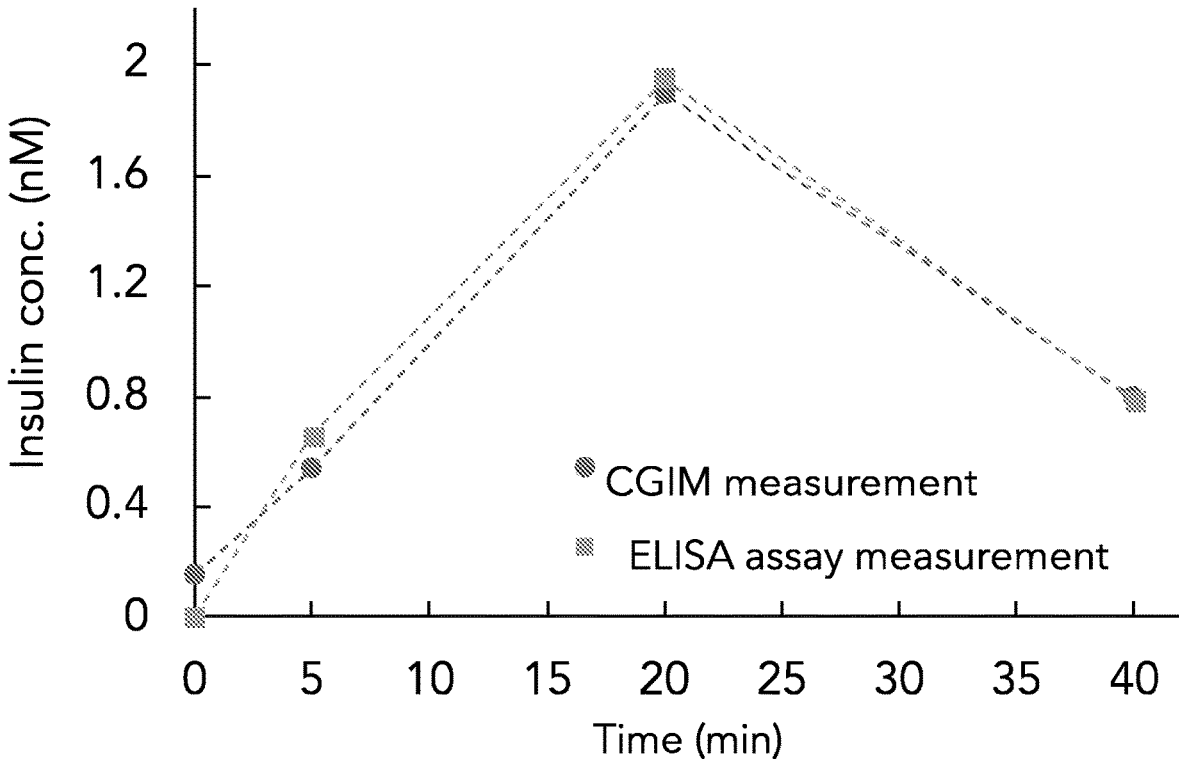

The glucose levels of anesthetized rats decreased less after insulin injection than in conscious rats. This is likely due to isoflurane treatment, which can result in increased glucose levels over time as well as increased insulin resistance at high glucose levels. To verify this hypothesis, the same amount of insulin was administered to a conscious rat and collected blood samples at t=0, 5, 20, and 40 min after injection. The RTCM device was then employed to measure glucose (FIG. 6A) and insulin (FIG. 6B) levels. A drop in glucose concentration was observed both in the glucose meter measurements and in the RTCM device, with a 7 mM decrease in glucose level after 40 minutes. These results clearly demonstrate the expected effect of insulin on glucose levels, and confirm the confounding effects of anesthesia on glucose levels in in vivo experiments that employ anesthetized rats. However, the latter was a necessity in order to test the RTCM platform's capacity to perform continuous measurement.

Example 4

Continuous, In-Vivo Tracking of Different Insulin Formulations

Differentiation between the pharmacokinetics of different insulin formulations was next tested. Specifically, the kinetics of Humulin R and Humulin N (neutral protamine Hagedorn) human insulins were compared. Humulin R is a short-acting insulin and has relatively short duration of action while Humulin N is an intermediate-acting insulin formulation, which was designed with delayed onset and extended duration of action as an early basal insulin replacement. Prior to the injection, the baseline was measured for 5 mins, then diabetic rats were injected either with Humulin R or Humulin N and the glucose and insulin concentrations were quantified over the course of 85 mins (FIG. 7). The different pharmacokinetics of Humulin R and Humulin N was clearly evident in the RTCM measurement: we noticeably detected that the Humulin R and Humulin N injection resulted in peaks approximately 15 mins and 60 mins after injection, respectively.

The above Examples demonstrate a real-time biosensor in a miniaturized, microfluidic device format that can continuously and simultaneously measure the concentration of molecules in a living subject with excellent sensitivity and less than a minute temporal resolution.

Example 5

Continuous Signal Amplification and Staged Incubation Methods

The present Example builds on Examples 1-4 in which a microfluidic device was developed and used to continuously detect and quantify glucose and insulin in live diabetic rats.

As described above, bead-based aptamer and antibody fluorescent assays with optical readout to simultaneously measure glucose and insulin. These assays were performed within a three-stage microfluidic device which (1) made use of chaotic mixing to accelerate binding kinetics, (2) made use of deterministic lateral displacement (DLD) to separate beads from blood components, and (3) focused beads into the field of view of a free-space fluorescent microscope. The present Example includes three advancements relative to Examples 1-4: (1) continuous signal amplification via Hybridization Chain Reaction (HCR) to allow for detection of low abundance proteins, (2) staged incubation in the microfluidic device to optimize assay performance, and (3) device configurations for both an intermittent and continuous mode.

A. HCR Amplified Real Time Assay

Figure 8:
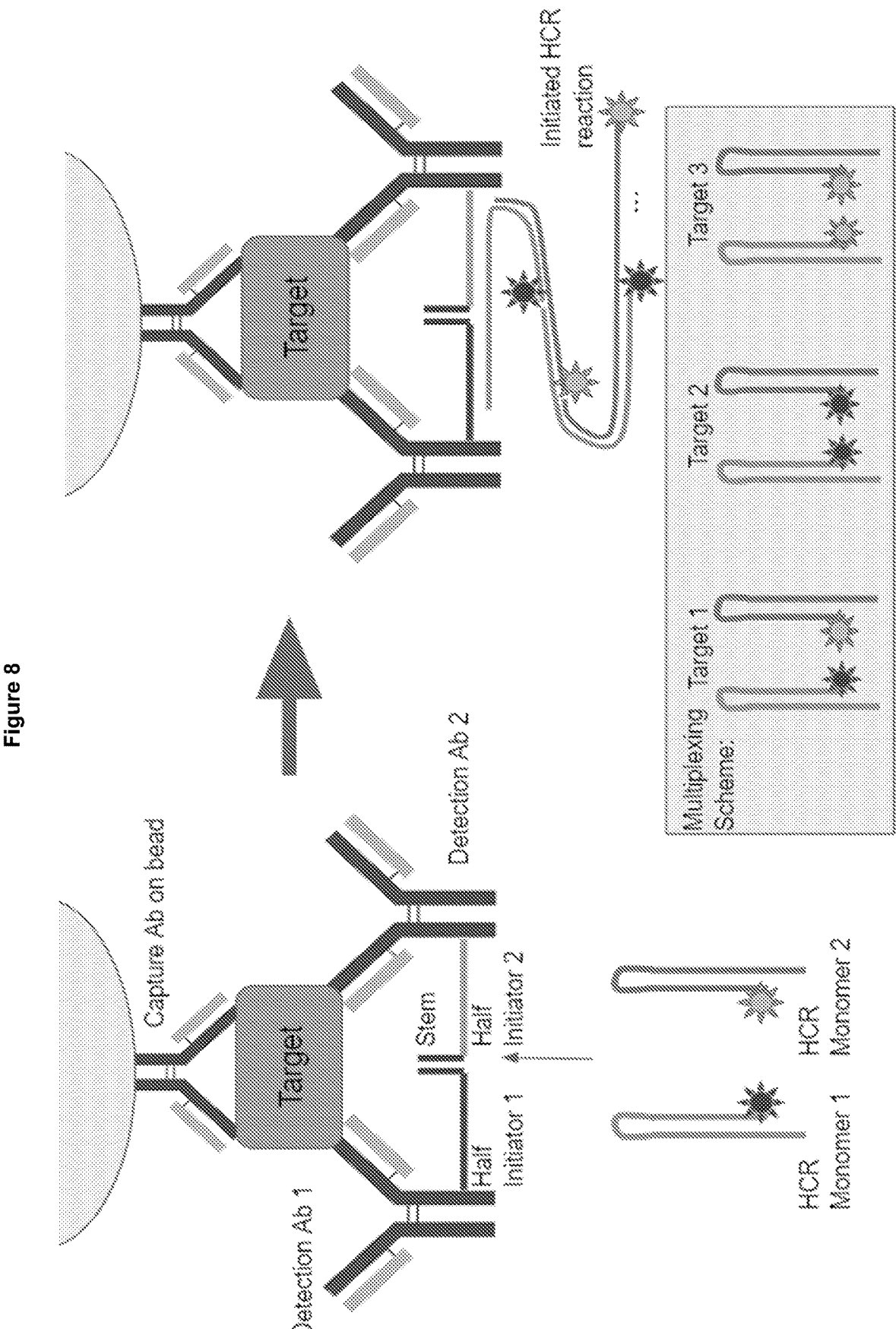
FIG. 8 shows a schematic for the HCR-Amplified Real Time Assay. Target binding on capture antibody-modified beads leads to the colocalization of two oligo-labeled detection antibodies. The stem regions of the colocalized oligos hybridize, effectively joining the two half initiator sequences. The full initiator sequence can then generate an HCR reaction that transduces the binding event into a fluorescent signal. Target multiplexing can be achieved with target-specific HCR reactions and monomers labeled with different fluorophore combinations.

The assay front end consists of a polyclonal three-antibody sandwich. Beads are coated with capture antibody. Two polyclonal detection antibodies are labeled with oligos consisting of two regions: a 'half initiator' region and a short 'stem' region (FIG. 8). The stem regions on the two detection antibodies are complementary such that in the presence of the target, the sandwich forms and the complementary stem regions hybridize, effectively joining the two half initiators together to form the full initiator sequence. Two additional fluorescently-labeled oligos (HCR monomer 1 and 2) are then added to the assay. These sequences are kinetically trapped in hairpin conformation and are metastable in solution. In the presence of the full initiator sequence, monomer 1 undergoes a displacement reaction that releases the hairpin and initiates a hybridization chain reaction with monomer 2. The reaction continues to extend until all available monomers are incorporated in the chain. This extension only occurs when the initiator regions from both antibody oligos are joined into one sequence, forming the full initiator sequence.

The stem region of the antibody oligos is designed with a relatively high KD, such that hybridization and HCR initiation can only occur when the antibodies are colocalized onto the target and have high effective concentrations. Thus, the thermodynamics of the stem region are tuned to be sufficiently weak to prevent detection antibody duplex formation in solution, but sufficiently stable to readily initiate HCR when colocalized onto the target . This assay achieves exquisite sensitivity and reduced background by requiring the colocalization of two distinct detection antibodies before generating any detectable signal and then amplifies that single binding event into a large fluorescent signal. Proximity initiation of amplification also implies that the assay can function without the need for washes between antibody binding and signal amplification because unwashed, uncolocalized antibodies won't initiate amplifications. By comparison, traditional ELISA assays require washes before substrate addition, to prevent amplification from nonspecifically-bound antibody probes.

Target multiplexing is achieved by designing unique HCR initiator and monomer sequences for each target in the assay. The identity of the target can then be encoded in the fluorescent reporters conjugated to the HCR monomers. For example, a three-plex assay can be implemented using only two fluorophores by labeling both monomers for the first target in one color, both monomers for the second target in another color, and finally labeling each monomer for the third target in different colors. By monitoring beads in both fluorescent channels simultaneously, the identity of the target captured by each bead can be easily deconvoluted.

Amplification Assay—Methods

Figure 9:
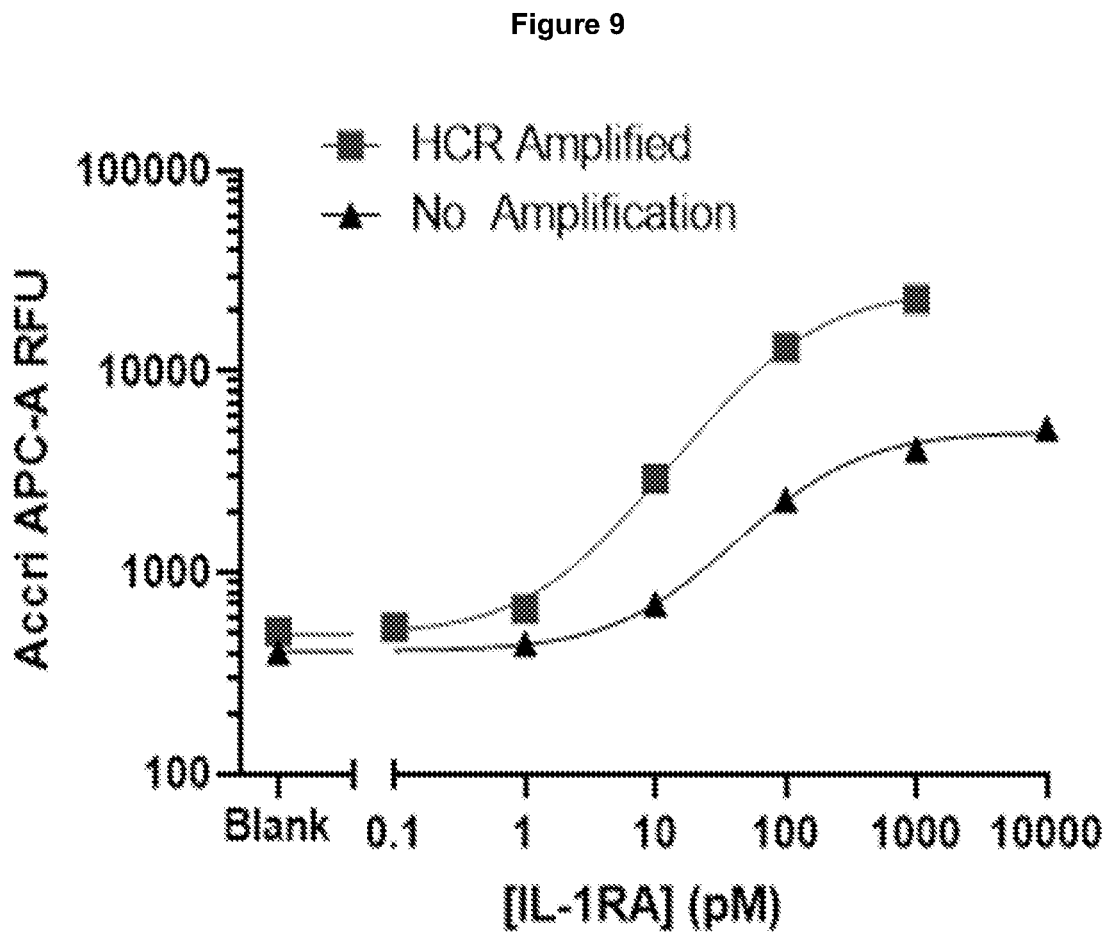

To obtain the 'HCR Amplified' results in FIG. 9 above, 250 ug of magnetic streptavidin 1 um beads (Thermo Fisher MyOne T1) were washed and incubated with 50 uL of 500 nM solution of biotinylated anti-IL-1RA polyclonal antibody (R&D systems) for 1 h with rotation. The beads were then washed several times to remove unbound antibody. These antibody-coated beads are denoted as capture beads.

Two separate stocks of native anti-IL-1RA polyclonal antibody (R&D systems) were conjugated with two distinct oligo sequences via Hydrazine-Aldehyde conjugation chemistry (Vector Laboratories SoluLink). These two sequences are termed Antibody Adapter 1 and Antibody Adapter 2—the antibody-oligo conjugates realized with these two sequences are termed Antibody 1 and Antibody 2 (Ab1, Ab2), respectively.

The sequences are as follows:

```
Antibody Adapter 1 (SEQ ID NO: 3):
CGTTGGATTATGCCCGACGC-Amine

Antibody Adapter 2 (SEQ ID NO: 4):
Amine-CGTCCTAGCCTGATAGGAAC
```

Ab1 was then incubated with another oligo termed Arm 1 (GCGTCGGGCATAATCCAACGGTCCCTGCCTC-TATATCTTTGAACGC; SEQ ID NO: 5), and Ab2 was incubated with Arm 2 (GCGTTCTTCCACTCAACTT-TAACCCGGTTCCTATCAGGCTAGGACG; SEQ ID NO: 6). These incubations were carried out at an excess of 10 Arm oligos: 1 Ab. Oligos Arm 1 and Arm 2 are partially-complementary to Adapter 1 and Adapter 2, respectively, such that when incubated with the antibody-oligo conjugates Ab1 and Ab2, Arm 1 and Arm 2 will hybridize to the Adapter sequences. In addition to Adapter-complementary regions, Arms 1 and 2 contain half of the HCR Initiator sequence and a 6 bp stem region complementary to the other arm's stem region. The assembled antibody-adapter-arm constructs were denoted as detection probes (FIG. 10, left). Detection probes 1 and 2 are shown colocalized onto a target molecule in FIG. 8—in that figure, adapter sequences were omitted for simplicity.

IL-1RA target was diluted to several different concentrations in Assay Buffer (1× phosphate buffered saline, 1 mg/mL bovine serum albumin, 0.05% Tween 20, 0.015 mg/mL goat IgG, 0.1 mg/mL salmon sperm DNA, 5 mM EDTA). 0.35 ug of beads were injected in 20 uL of each target dilution. The solutions were incubated on a rotator for 1 h 30 min to allow target proteins to be captured on the capture beads.

1 uM solutions of detection probe 1 and 2 were mixed together at a ratio of 1:1 to obtain a detection probe solution at 500 nM. 5 uL of detection probe solution were injected into each target tube and incubated for 1 h 30 min on a rotator to allow detection probes to co-localize on captured targets and for stems to hybridize, forming the full initiator sequence.

Finally, to initiate signal amplification, 2.7 uL of 10 uM solution of HCR Monomer 1 and 2 in HCR Reaction buffer (1× PBS, 10 mM MgCl2) were injected into each assay tube and incubated 15 minutes on a rotator. Following amplification, beads were washed once in wash buffer (1× PBS, 1 mM MgCl2) and imaged on a flow cytometer.

To obtain the 'No Amplification' results in FIG. 9, a similar procedure was followed. However, in the detection probe hybridization step, a fluorophore-labeled adapter beacon was hybridized in lieu of the arms oligos (FIG. 10, right). Also, the HCR monomer injection was skipped, and samples were washed and imaged on flow cytometer directly. Thus, the signal in this assay comes from direct fluorophore labeling of the antibodies.

B. Stage Incubation

RT-ELISA for glucose and insulin added all assay reagents to the sample at the beginning of the mixing module. In the present method, the increased assay complexity calls for an adjustment to integrated microfluidics. Capture-antibody-coated beads are first introduced with the sample in order to prioritize target capture onto beads. Detection antibodies are introduced in a second stage, initiating target labeling (detection antibody binding) only after capture has occurred. Simultaneous addition of both reagents would lead to rapid depletion of epitopes by the detection antibodies in solution, preventing the successful capture and pulldown of the target onto beads. HCR monomers are introduced in a third and final mixing stage to ensure that HCR is initiated after target labeling is completed.

Staged incubation has been verified by the sequential reagent addition described in the Amplification Assay Methods section herein.

C. Intermittent and Continuous Readout

Fundamentally, the methods and device in this exemplary embodiment requires an assay incubation stage, a bead separation stage to remove blood components, and an optical readout phase to measure concentration.

Continuous Mode

In the continuous mode of operation, the device leverages the same approach developed described in Examples 1-4: the assay is realized on 15 um polystyrene beads that are sorted from blood cells components in the DLD module based on their size. Sorting is done in real time, as the bead and blood sample mixture flows through the microfluidics. The recovered beads are focused into a single-bead stream using an inertial focusing module. In this focusing module, an asymmetric curved channel is designed to establish inertial forces under laminar flow conditions which drive beads to a single equilibrium point in the channel width. By establishing a single file bead flow condition, the fluorescence signals of beads can be individually quantified using a highly sensitive photon detector (e.g. multi-pixel photon counting module or single photon counting module) and variation in signal due to bead position in the channel is minimized. In the present mode, beads need not be imaged in two dimensions; rather, their fluorescence intensity must be quantified. Therefore, signal from individual beads may be coupled to the detector using either free-space optics or fiber optic waveguides. Additionally, the three-plex assay described above can be achieved by simultaneously monitoring two different fluorophore channels.

Intermittent Mode—1

In a first exemplary mode, an intermittent mode makes use of an identical device to that used in the continuous mode described herein. The only difference is the introduction of sample and the data processing. In the first exemplary intermittent mode, a single volume of blood (or other biological fluid as described herein) can be introduced to the device using a syringe pump rather than the peristaltic pump used for continuous blood sampling. Additionally, all bead signals will be measured and used to determine and report a single concentration for each biomarker, rather than a concentration that varies over time.

Intermittent Mode—2

In a second exemplary intermittent mode of operation, the real-time bead sorting DLD module is replaced with a magnetic pull-down chamber previously developed. The assay is realized on lum magnetic beads, such that after staged incubation in the mixing channel, beads can be separated from blood by means of a nickel mesh patterned on the substrate of the microfluidic module, magnetized by an external permanent magnet. Substrate-captured beads are subsequently washed with flowing buffer and imaged using a custom, compact fluorescent microscope with a readout camera mounted above the device. Multiplexing can be achieved by using several fluorescent channel filters and obtaining an image for each excitation/emission set. The device can be regenerated by demagnetizing the nickel grid and releasing the beads from the substrate.

This approach provides several advantages compared to the continuous-mode device. Firstly, smaller-size beads enable more efficient target capture due to better surface area and diffusive properties. This translates into better sensitivity or shorter incubation times. Secondly, the magnetic pull-down device can be easily washed and regenerated many times for multiple measurements taken over many hours.

This technology can be further multiplexed. The means of multiplexing include fluorescence-based expansions such as expanding HCR to use a three-monomer design, allowing for ratiometric labeling of targets (e.g. 2 green:1 red) and using additional fluorophores. Additionally, the assay can be realized on multiple bead sizes which can be sorted into separate detection streams to allow for further multiplexing.

Finally, the following publications relate to various technologies of HCR and microfluidic detection methods—Choi et al., Anal. Chem., 2011, 83(17)6890-6895; Ranallo, S., et al., Nature Comm., 2019, 10, 5509; Li et al., ChemComm., 2019, 55, 4387-4390; Koos, et al., Nature Comm., 2015, 7294; Chang et al., JACS, 2019, 141(32)12738-12743; Wang et al., anal. Chem., 2018, 90(24)14433-14438; Tang et al., anal. Chem., 2015, 87(16)8063-8066; Weng et al., Biosensors, 2016, 6(2)24; Cohen et al., Michrochimica Acta, 2017, 184, 835-841; Marschewski et al., Lab Chip, 2015, 15, 1923-1933; and McGrath et al., Lab on a Chip, 2014, 14, 4139-4158.

The various embodiments described above can be combined to provide further embodiments. All U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified if necessary to employ concepts of the various patents, applications, and publications to provide yet further embodiments.

These and other changes can be made to the embodiments in light of the above-detailed description. In general, in the following claims, the terms used should not be construed to limit the claims to the specific embodiments disclosed in the specification and the claims but should be construed to include all possible embodiments along with the full scope of equivalents to which such claims are entitled. Accordingly, the claims are not limited by the disclosure.

---

What is claimed is:

1. A method of determining continuous variations in concentration of molecular species in a living subject in real-time over a period of time, the method comprising:
    (a) introducing a biological fluid from the subject to a microfluidic device without interruption over a first period of time;
    (b) introducing a capture solution comprising a first affinity agent and optionally a first detection agent to the microfluidic device one or more times for one or more time periods during step (a);
    (c) forming a first complex by mixing the biological fluid and the capture solution under conditions whereby a first molecular species in the biological fluid contacts and binds the first affinity agent, and the optional first detection agent binds to the first molecular species bound to the first affinity agent in the biological fluid;
    (d) optionally depleting biological fluid components not bound to the first affinity agent after step (c);
    (e) detecting the first complex by detecting a detection signal from the first molecular species bound to the first affinity agent and optionally bound to the first detection agent; and
    (f) determining the continuous variation in the concentration of the first molecular species in the living subject in real-time over the first period of time.

2. The method of claim 1 wherein the determining in step (f) further comprises determining continuous variations in concentration of a second molecular species and up to a tenth molecular species.

3. The method of claim 1 wherein the first molecular species is selected from the group consisting of:
    a drug, neurotransmitter, a neurochemical, a protein, and a carbohydrate.

4. The method of claim 1 wherein said first affinity agent comprises an antibody or an aptamer.

5. The method of claim 4 wherein the first affinity agent further comprises a microbead.

6. The method of claim 5 wherein the aptamer is conjugated to the first detection agent.

7. The method of claim 5 wherein the antibody is conjugated to the microbead thereby enabling the antibody to bind to the first molecular species in the biological fluid and wherein the detection agent is capable of binding the first molecular species in the biological fluid.

8. The method of claim 7 wherein the first detection agent comprises a fluorophore.

9. The method of claim 1 wherein the first affinity agent is capable of forming the first complex with the first molecular species and with a second molecular species, the first detection agent is capable of forming a second complex with the first affinity agent and a second detection agent and the capture solution further comprises:
    a second affinity agent capable of forming a third complex with athird molecular species and a fourth molecular species, and the second detection agent is capable of forming a fourth complex with a third affinity agent and a fourth affinity agent.

10. The method of claim 1 wherein the biological fluid is selected from the group consisting of whole blood, serum, plasma, interstitial fluid, saliva, urine, and cerebrospinal fluid.

11. The method of claim 1 wherein the microfluidic device comprises a lane comprising a mixing module for performing step (c), and optionally a depletion module for performing step (d), and a detection module for performing step (e).

12. The method of claim 11 wherein the lane has a serpentine shape.

13. The method of claim 12 wherein the mixing in step (c) takes less than a minute.

14. The method of claim 12 wherein the depletion module comprises a plurality of posts for depleting the biological fluid components not bound by the first affinity agent.

15. The method of claim 14 wherein the depleting in step (d) takes less than 30 seconds.

16. The method of claim 11 wherein the detection module comprises an image-capturing device capable of detecting the first complex.

17. The method of claim 1 wherein the microfluidic device is operably attached to a surface of the subject.

18. A method of treating a disease of a disorder of a subject, said method comprising
    (a) introducing a biological fluid from the subject to a microfluidic device without interruption over a first period of time;
    (b) introducing a capture solution comprising a first affinity agent and optionally a first detection agent to the microfluidic device one or more times for one or more time periods during step (a);
    (c) forming a first complex by mixing the biological fluid and the capture solution under conditions whereby a first molecular species in the biological fluid contacts and binds the first affinity agent, and the optional first detection agent binds to the first molecular species bound to the first affinity agent in the biological fluid;
    (d) optionally depleting biological fluid components not bound to the first affinity agent after step (c);
    (e) detecting the first complex by detecting a detection signal from the first molecular species bound to the first affinity agent and optionally bound to the first detection agent;
    (f) determining the continuous variation in the concentration of the first molecular species the living subject in real-time over the first period of time; and
    (g) treating the subject by administering a therapeutic agent intermittently or without interruption over the period of time based on the determined continuous variations in the concentration of the first molecular species in the living subject in real-time over the period of time, wherein the first molecular species is associated with the disease or the disorder, thereby treating said subject.

19. The method of claim 1, further comprising amplifying the detection signal, wherein said amplifying comprises administering a composition comprising a plurality of amplification agents.

20. The method of claim 19, wherein the plurality of amplification agents comprises:

(1) a first antibody conjugated with a first oligonucleotide capable of at least partially hybridizing, the first antibody capable of binding to a target molecule;

(2) a second antibody conjugated with a second oligonucleotide capable of at least partially hybridizing, the second antibody capable of binding to the target molecule;

(3) a third oligonucleotide conjugated with a first detection label;

(4) a forth oligonucleotide conjugated with a second detection label;

wherein said plurality of amplification agents is capable of undergoing a hybridization chain reaction.

\*    \*    \*    \*    \*

SEQUENCE LISTING

<160> NUMBER OF SEQ ID NOS: 6

<210> SEQ ID NO 1
<211> LENGTH: 51
<212> TYPE: DNA

-continued

```
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: 5Biosg
<220> FEATURE:
<221> NAME/KEY: misc_feature
<222> LOCATION: (1)..(1)
<223> OTHER INFORMATION: iCy5

<400> SEQUENCE: 1
ctctcgggac gaccgtgtgt gttgctctgt aacagtgtcc attgtcgtcc c          51

<210> SEQ ID NO 2
<211> LENGTH: 14
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (14)..(14)
<223> OTHER INFORMATION: 3BHQ2

<400> SEQUENCE: 2
ggtcgtcccg agag                                                   14

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (20)..(20)
<223> OTHER INFORMATION: Amine

<400> SEQUENCE: 3
cgttggatta tgcccgacgc                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (1)..(1)
<223> OTHER INFORMATION: Amine

<400> SEQUENCE: 4
cgtcctagcc tgataggaac                                             20

<210> SEQ ID NO 5
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 5
gcgtcgggca taatccaacg gtccctgcct ctatatcttt gaacgc               46

<210> SEQ ID NO 6
<211> LENGTH: 46
```

-continued

```
<212> TYPE: DNA
<213> ORGANISM: Artificial Sequence
<220> FEATURE:
<223> OTHER INFORMATION: Synthetic Polynucleotide

<400> SEQUENCE: 6
gcgttcttcc actcaacttt aacccggttc ctatcaggct aggacg                      46
```